(12) United States Patent
Sharp

(10) Patent No.: US 11,246,872 B2
(45) Date of Patent: Feb. 15, 2022

(54) TOPICAL ACYCLOVIR FORMULATIONS AND USES THEREOF

(71) Applicant: PROPELLA THERAPEUTICS, INC., Pittsboro, NC (US)

(72) Inventor: Matthew J. Sharp, Apex, NC (US)

(73) Assignee: Propella Therapeutics, Inc., Pittsboro, NC (US)

( * ) Notice: Subject to any disclaimer, the term of this patent is extended or adjusted under 35 U.S.C. 154(b) by 0 days.

(21) Appl. No.: 16/899,952

(22) Filed: Jun. 12, 2020

(65) Prior Publication Data

US 2020/0390773 A1 Dec. 17, 2020

Related U.S. Application Data

(60) Provisional application No. 62/861,637, filed on Jun. 14, 2019.

(51) Int. Cl.

| | |
|---|---|
| *A01N 37/00* | (2006.01) |
| *A61K 31/215* | (2006.01) |
| *A01N 37/12* | (2006.01) |
| *A01N 37/44* | (2006.01) |
| *A61K 31/24* | (2006.01) |
| *A01N 25/00* | (2006.01) |
| *A61K 31/522* | (2006.01) |
| *A61K 9/00* | (2006.01) |
| *A61K 9/06* | (2006.01) |
| *A61K 47/10* | (2017.01) |

(52) U.S. Cl.
CPC .......... *A61K 31/522* (2013.01); *A61K 9/0014* (2013.01); *A61K 9/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,499,084 A | 2/1985 | Dixon | |
| 4,963,555 A | 10/1990 | Jones et al. | |
| 5,585,379 A * | 12/1996 | Sintov | A61K 31/70 514/263.38 |
| 6,337,324 B1 | 1/2002 | Harmenberg et al. | |
| 6,596,763 B1 | 7/2003 | Thormar et al. | |
| RE39,264 E | 9/2006 | Harmenberg et al. | |
| 7,223,387 B2 | 5/2007 | Lekare | |
| 8,633,169 B2 | 1/2014 | Caramella et al. | |
| 8,771,712 B2 | 7/2014 | Dinh et al. | |
| 9,144,576 B2 | 9/2015 | Brown et al. | |
| 9,468,644 B2 | 10/2016 | Kalem | |
| 9,827,315 B2 | 11/2017 | Patel et al. | |
| 10,085,994 B2 | 10/2018 | Lozinsky et al. | |
| 2018/0071390 A1 | 3/2018 | Patel et al. | |
| 2019/0046438 A1 | 2/2019 | Hnat | |

FOREIGN PATENT DOCUMENTS

| | | | |
|---|---|---|---|
| CN | 1235547 A * | 11/1999 | .............. A61P 31/22 |
| EP | 1762226 A2 | 3/2007 | |
| WO | WO 9415614 A1 | 7/1994 | |

OTHER PUBLICATIONS

Bodenlenz, M., et al., "Open Flow Microperfusion as a Dermal Pharmacokinetic Approach to Evaluate Topical Bioequivalence," Clin Pharmacokinet., 56:91-98 (2017).
FDA Workshop on Bioequivalence Testing of Topical Drug Products Presentation, "Correlation of physiochemical characteristics and in vitro permeation test (IVPT) results for acyclovir and metronidazole topical products," Silver Spring, MD, U.S.A., Oct. 20, 2017.
Partial search result and accompanying provisional opinion issued in PCT/US2020/037421, dated Sep. 21, 2020.
Zovirax (acyclovir) Cream Prescribing Label, Reference ID: 3481551, revised Apr. 2014.

* cited by examiner

*Primary Examiner* — Layla Soroush
(74) *Attorney, Agent, or Firm* — Nixon & Vanderhye P.C.

(57) ABSTRACT

Provided herein are gel formulations of acyclovir with a low concentration of acyclovir, which can be used, for example, for the treatment of recurrent herpes labialis (cold sores) in immunocompetent adults and adolescents 12 years of age and older. The gel formulation can be an aqueous gel formulation, an emulsified gel formulation, or a non-aqueous gel formulation.

4 Claims, 6 Drawing Sheets

TOPICAL ACYCLOVIR FORMULATIONS AND USES THEREOF

Figure 1:
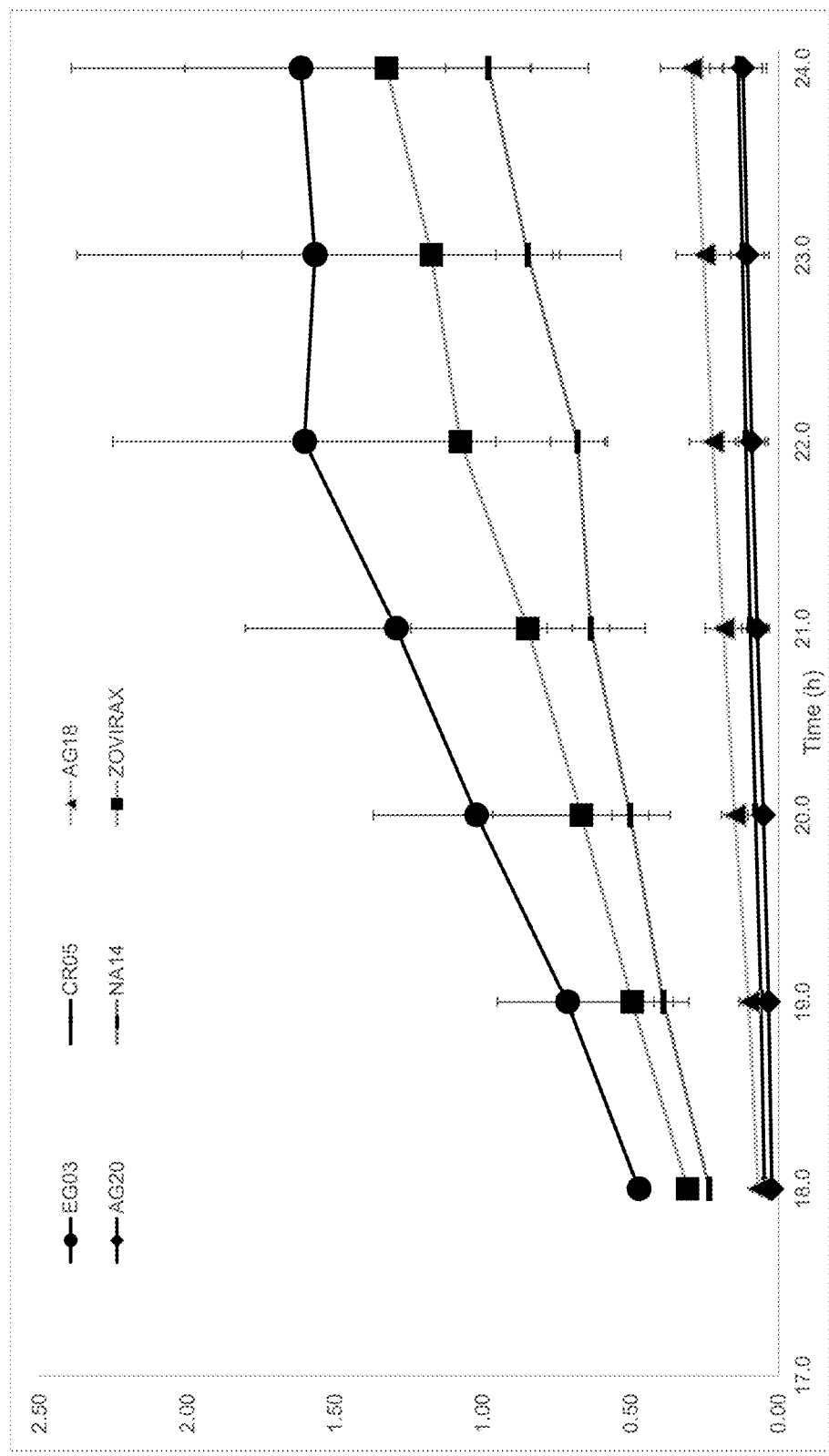

This application claims the benefit of U.S. Provisional Application No. 62/861,637, filed Jun. 14, 2019, the content of which is incorporated herein by reference in its entirety.

BACKGROUND

In various embodiments, the present disclosure is generally related to antiviral compositions and methods.

BACKGROUND ART

Herpes labialis is an infection of the lips or perioral area. The primary infection is usually asymptomatic; however, it can also present itself as herpes simplex virus (HSV) gingivostomatitis. Herpes labialis can be caused by either HSV type 1 (HSV-1) or HSV type 2 (HSV-2), although recurrences are almost always caused by HSV-1. In most patients, fewer than two recurrences of herpes labialis manifest each year, but some individuals have monthly recurrences.

Acyclovir is a synthetic purine nucleoside analogue with inhibitory activity against HSV-1, HSV-2, and varicella-zoster virus (VZV). This inhibitor activity is highly selective due to its affinity for the enzyme thymidine kinase (TK). This enzyme converts acyclovir into acyclovir monophosphate, a nucleoside analogue. This molecule is further converted into a diphosphate and then into a triphosphate. Acyclovir triphosphate stops replication of herpes viral DNA. This is accomplished in three ways: first, by competitive inhibition of viral DNA polymerase; second, by incorporation into viral DNA leading to termination of growing viral DNA chains; and third, by inactivation of viral DNA polymerase. This phosphorylation is done more efficiently by HSV than by VZV; therefore, a greater antiviral activity against HSV exists.

An acyclovir-containing product has already been approved (Zovirax® Cream 5%) for treating recurrent herpes labialis (cold sores) in immunocompetent adults and adolescents 12 years of age and older through topical administration. Zovirax® Cream 5% has several short comings, such as poor solubility of the drug in the commercial product (<0.5%), large particle range of acyclovir, and poor permeability.

BRIEF SUMMARY

In various embodiments, the present disclosure provides a gel formulation of acyclovir with a low concentration of acyclovir, which can be used, for example, for the treatment of herpes viral infections such as those caused by HSV-1 and/or HSV-2, or varicella-zoster virus (VZV) infection, including recurrent herpes labialis (cold sores) in immunocompetent adults and adolescents 12 years of age and older. The gel formulations of the present disclosure have several advantages over the marketed product Zovirax® Cream 5%, for example, improved skin penetration and better patient compliance. With an improved skin penetration, even though at a far lower level of acyclovir, the gel formulation of the present disclosure delivers as much acyclovir into the skin as the marketed product Zovirax® Cream 5%.

The gel formulation of the present disclosure can be an aqueous gel (non-emulsified gel) formulation, emulsified gel formulation, or a non-aqueous gel formulation.

Some embodiments of the present disclosure are directed to an aqueous gel formulation. In some embodiments, the aqueous gel formulation comprises acyclovir dissolved or partially suspended in an aqueous gel, wherein the acyclovir is in an amount of about 0.05% to about 0.5% by weight of the aqueous gel formulation, wherein the aqueous gel comprises a solvent system and an effective amount of a gel-forming agent, wherein the solvent system comprises water in an amount of about 20% to about 80% by weight of the aqueous gel formulation, and one or more water-miscible organic solvents in an amount of about 15% to about 70% by weight of the aqueous gel formulation; and wherein the aqueous gel formulation is formulated for topical use. In some embodiments, the one or more water-miscible organic solvents are selected from propylene glycol, glycerol, Transcutol® (diethylene glycol monoethyl ether), dimethyl sulfoxide (DMSO), a low molecular weight polyethylene glycol (e.g., PEG 400) and combinations thereof. In some embodiments, the one or more water-miscible organic solvents comprise Transcutol® in an amount of about 10% to about 60% by weight. In some embodiments, the one or more water-miscible organic solvents comprise propylene glycol in an amount of about 5% to about 30% by weight. In some embodiments, the one or more water-miscible organic solvents comprise a low molecular weight polyethylene glycol in an amount of about 5% to about 40% by weight. In some embodiments, the low molecular weight polyethylene glycol is polyethylene glycol 400. In some embodiments, the one or more water-miscible organic solvents are free or substantially free of DMSO. The pH of the aqueous gel formulation is typically about 4-8. In some embodiments, acyclovir is the only active ingredient. In some embodiments, the aqueous gel formulation further comprises an antioxidant or preservative. In some embodiments, the antioxidant or preservative is selected from butylated hydroxytoluene, phenoxyethanol, sodium metabisulfite, EDTA, ascorbic acid, and combinations thereof. In some embodiments, the gel-forming polymer is a crosslinked polyacrylic acid (e.g., a carbopol homopolymer, Carbopol® 980, which is a crosslinked polyacrylic acid with allyl sucrose or allyl pentaerythritol, polymerized in a cosolvent containing ethyl acetate and cyclohexane, with a viscosity range of about 40,000-60,000 cP (0.5% weight at pH 7.5), available from the Lubrizol Corporation). Further characteristics of the aqueous gel formulation are described herein.

In some embodiments, the gel formulation is an emulsified gel formulation. In some embodiments, the emulsified gel formulation comprises acyclovir dissolved or partially suspended in an emulsified gel, wherein the acyclovir is in an amount of about 0.05% to about 0.5% by weight of the emulsified gel formulation, wherein the emulsified gel comprises a solvent system, an oil, an emulsifier and an effective amount of a gel-forming agent; wherein the solvent system comprises water in an amount of about 20% to about 80% by weight of the emulsified gel formulation; and one or more water-miscible organic solvents in an amount of about 15% to about 70% by weight of the emulsified gel formulation; and wherein the emulsified gel formulation is formulated for topical use. In some embodiments, the one or more water-miscible organic solvents are selected from propylene glycol, glycerol, Transcutol®, dimethyl sulfoxide (DMSO), a low molecular weight polyethylene glycol (e.g., PEG 400) and combinations thereof. In some embodiments, the oil in the emulsified gel comprises an emollient, such as a fatty ester (e.g., mixed esters/triglycerides of palm oil or coconut oil, such as Crodamol™ GTCC (caprylic/capric triglyceride), a mixed ester consisting primarily of caprylic (C8) and capric (C10) acids derived from either coconut or palm oil, available from Croda Inc.), e.g., in an amount of about 1% to about 20% by weight of the emulsified gel formulation. In some embodiments, the emulsifier comprises an acrylamide and acryloyldimethyl taurate copolymer and a non-ionic surfactant. In some embodiments, the emulsifier comprises an acrylamide and sodium acryloyldimethyl taurate copolymer dispersed in isohexadecane and a non-ionic surfactant (e.g., polysorbate, such as polysorbate 80), e.g., Sepineo™ P 600 (acrylamide and sodium acryloyldimethyl taurate copolymer dispersed in isohexadecane and polysorbate 80, available from Seppic S.A.). In some embodiments, the emulsifier is in an amount of about 1% to about 10% by weight of the emulsified gel formulation. In some embodiments, the emulsifier is also a gel-forming agent. In some embodiments, the emulsifier is different from the gel-forming agent. Further characteristics of the emulsified gel formulation are described herein.

Some embodiments of the present disclosure are directed to a non-aqueous gel formulation comprising acyclovir dissolved or partially suspended in a non-aqueous gel, wherein the acyclovir is in an amount of about 0.05% to about 0.5% by weight of the non-aqueous gel formulation, wherein the non-aqueous gel comprises a solvent system and an effective amount of a gel-forming agent, wherein the solvent system comprises one or more solvents selected from propylene glycol, glycerol, Transcutol®, dimethyl sulfoxide (DMSO), a low molecular weight polyethylene glycol, and combinations thereof and wherein the non-aqueous gel formulation is formulated for topical use. Further characteristics of the non-aqueous gel formulation are described herein.

The gel formulation of the present disclosure can also be characterized by certain permeation profile. For example, in some embodiments, the aqueous gel or emulsified gel formulation topically delivers acyclovir to a subject/user at a permeation rate per unit area of about 20% to about 500% of that of a dose equivalent cream or gel formulation containing 5% acyclovir by weight. The gel formulation of the present disclosure is typically shelf stable.

Some embodiments of the present disclosure are also directed to methods of treating or preventing herpes labialis in a subject in need thereof. In some embodiments, the method comprises topically applying to the subject an effective amount of the gel formulation of the present disclosure.

Some embodiments of the present disclosure are also directed to methods of treating or preventing herpes viral infections of the skin or mucosa in a subject in need thereof. In some embodiments, the method comprises topically applying to the subject an effective amount of the gel formulation of the present disclosure. In some embodiments, the herpes viral infection is herpes simplex virus (HSV) infection. In some embodiments, the herpes viral infection is HSV-1 and/or HSV-2 infection. In some embodiments, the herpes infection is varicella-zoster virus (VZV) infection. In some embodiments, the herpes viral infection is a herpes zoster infection. In some embodiments, the herpes viral infection is herpes varicella infection.

Some embodiments of the present disclosure are also directed to methods of treating or preventing one or more diseases selected from genital herpes simplex, neonatal herpes simplex, cold sores, shingles, acute chickenpox (e.g., in immunocompromised patients), acute mucocutaneous HSV infections (e.g., in immunocompromised patients), herpes of the eye, and herpes simplex blepharitis. In some embodiments, the method comprises topically applying to a subject in need thereof an effective amount of the gel formulation of the present disclosure.

In some embodiments, the present disclosure provides:

[1] An aqueous gel formulation comprising acyclovir dissolved or partially suspended in an aqueous gel,
  wherein the acyclovir is in an amount of about 0.05% to about 5%, such as about 0.05% to about 0.5% by weight of the aqueous gel formulation,
  wherein the aqueous gel comprises a solvent system and an effective amount of a gel-forming agent,
  wherein the solvent system comprises water in an amount of about 20% to about 80% by weight of the aqueous gel formulation; and one or more water-miscible organic solvents in an amount of about 15% to about 70% by weight of the aqueous gel formulation; and
  wherein the aqueous gel formulation is formulated for topical use.

[2] The aqueous gel formulation of [1], wherein the one or more water-miscible organic solvents are selected from propylene glycol, glycerol, Transcutol®, dimethyl sulfoxide (DMSO), a low molecular weight polyethylene glycol, and combinations thereof

[3] The aqueous gel formulation of [1] or [2], wherein the one or more water-miscible organic solvents comprise Transcutol® in an amount of about 10% to about 60% by weight.

[4] The aqueous gel formulation of any one of [1]-[3], wherein the one or more water-miscible organic solvents comprise propylene glycol in an amount of about 5% to about 30% by weight.

[5] The aqueous gel formulation of any one of [1]-[4], wherein the one or more water-miscible organic solvents comprise a low molecular weight polyethylene glycol in an amount of about 5% to about 40% by weight.

[6] The aqueous gel formulation of [5], wherein the low molecular weight polyethylene glycol is polyethylene glycol 400.

[7] The aqueous gel formulation of any one of [1]-[6], wherein the one or more water-miscible organic solvents are free or substantially free of DMSO.

[8] The aqueous gel formulation of any one of [1]-[7], wherein the gel-forming agent is a crosslinked polyacrylic acid (e.g., a crosslinked polyacrylic acid with allyl sucrose or allyl pentaerythritol such as Carbopol® 980).

[9] The aqueous gel formulation of any one of [1]-[8], wherein the pH of the aqueous gel formulation is about 4 to 8.

[10] The aqueous gel formulation of any one of [1]-[9], wherein acyclovir is the only active ingredient.

[11] The aqueous gel formulation of any one of [1]-[10], further comprising an antioxidant or preservative.

[12] The aqueous gel formulation of [11], wherein the antioxidant or preservative is selected from butylated hydroxytoluene, phenoxyethanol, sodium metabisulfite, EDTA, ascorbic acid, and combinations thereof

[13] The aqueous gel formulation of any one of [1]-[12], which topically delivers acyclovir to a subject/user at a permeation rate per unit area of about 20% to about 500-fold greater than that of a dose equivalent cream or gel formulation containing 5% acyclovir by weight.

[14] The aqueous gel formulation of any one of [1]-[13], which is shelf stable.

[15] An emulsified gel formulation comprising acyclovir dissolved or partially suspended in an emulsified gel,
wherein the acyclovir is in an amount of about 0.05% to about 5%, such as about 0.05% to about 0.5% by weight of the emulsified gel formulation,
wherein the emulsified gel comprises a solvent system, an oil, an emulsifier and an effective amount of a gel-forming agent,
wherein the solvent system comprises water in an amount of about 20% to about 80% by weight of the emulsified gel formulation; and one or more water-miscible organic solvents in an amount of about 15% to about 70% by weight of the emulsified gel formulation; and
wherein the emulsified gel formulation is formulated for topical use.

[16] The emulsified gel formulation of [15], wherein the one or more water-miscible organic solvents are selected from propylene glycol, glycerol, Transcutol®, dimethyl sulfoxide (DMSO), a low molecular weight polyethylene glycol, and combinations thereof

[17] The emulsified gel formulation of [15] or [16], wherein the one or more water-miscible organic solvents comprise Transcutol® in an amount of about 10% to about 60% by weight.

[18] The emulsified gel formulation of any one of [15]-[17], wherein the one or more water-miscible organic solvents comprise propylene glycol in an amount of about 5% to about 30% by weight.

[19] The emulsified gel formulation of any one of [15]-[18], wherein the one or more water-miscible organic solvents comprise a low molecular weight polyethylene glycol in an amount of about 5% to about 40% by weight.

[20] The emulsified gel formulation of [19], wherein the low molecular weight polyethylene glycol is polyethylene glycol 400.

[21] The emulsified gel formulation of any one of [15]-[20], wherein the one or more water-miscible organic solvents are free or substantially free of DMSO.

[22] The emulsified gel formulation of any one of [15]-[21], wherein the oil is an emollient, such as a fatty ester (e.g., a triglyceride of caprylic and/or capric acid or a mixed ester of palm oil or coconut oil, such as Crodamol™ GTCC), e.g., in an amount of about 1% to about 20% by weight of the emulsified gel formulation.

[23] The emulsified gel formulation of any one of [15]-[22], wherein the emulsifier comprises an acrylamide and acryloyldimethyl taurate copolymer and a non-ionic surfactant, e.g., an acrylamide and sodium acryloyldimethyl taurate copolymer dispersed in isohexadecane and a non-ionic surfactant (e.g., polysorbate, such as polysorbate 80), e.g., Sepineo™ P 600.

[24] The emulsified gel formulation of [23], wherein the emulsifier is in an amount of about 1% to about 10% by weight of the emulsified gel formulation.

[25] The emulsified gel formulation of any one of [15]-[24], wherein the pH of the emulsified gel formulation is about 4 to 8.

[26] The emulsified gel formulation of any one of [15]-[25], wherein acyclovir is the only active ingredient.

[27] The emulsified gel formulation of any one of [15]-[26], further comprising an antioxidant or preservative.

[28] The emulsified gel formulation of [27], wherein the antioxidant or preservative is selected from butylated hydroxytoluene, phenoxyethanol, sodium metabisulfite, EDTA, ascorbic acid, and combinations thereof

[29] The emulsified gel formulation of any one of [15]-[28], which topically delivers acyclovir to a subject/user at a permeation rate per unit area of about 20% to about 500-fold greater than that of a dose equivalent cream or gel formulation containing 5% acyclovir by weight.

[30] The emulsified gel formulation of any one of [15]-[29], which is shelf stable.

[31] A non-aqueous gel formulation comprising acyclovir dissolved or partially suspended in a non-aqueous gel,
wherein the acyclovir is in an amount of about 0.05% to about 5% such as about 0.05% to about 0.5% by weight of the non-aqueous gel formulation,
wherein the non-aqueous gel comprises a solvent system and an effective amount of a gel-forming agent,
wherein the solvent system comprises one or more solvents selected from propylene glycol, glycerol, Transcutol®, dimethyl sulfoxide (DMSO), a low molecular weight polyethylene glycol, and combinations thereof; and
wherein the non-aqueous gel formulation is formulated for topical use.

[32] A method of treating or preventing herpes labialis in a subject in need thereof comprising topically applying to the subject an effective amount of the aqueous gel formulation of any one of [1]-[14], the emulsified gel formulation of any one of [15][30], or the non-aqueous gel formulation of [31].

[33] A method of treating or preventing herpes viral infections of the skin or mucosa of a subject in need thereof comprising topically applying to the subject an effective amount of the aqueous gel formulation of any one of [1]-[14], the emulsified gel formulation of any one of [15]-[30], or the non-aqueous gel formulation of [31].

[34] A method of treating or preventing herpes zoster infections of the skin or mucosa of a subject in need thereof comprising topically applying to the subject an effective amount of the aqueous gel formulation of any one of [1]-[14], the emulsified gel formulation of any one of [15]-[30], or the non-aqueous gel formulation of [31].

[35] A method of treating or preventing herpes varicella infections of the skin or mucosa of a subject in need thereof comprising topically applying to the subject an effective amount of the aqueous gel formulation of any one of [1]-[14], the emulsified gel formulation of any one of [15]-[30], or the non-aqueous gel formulation of [31].

[36] An aqueous gel formulation comprising: a) acyclovir in an amount of about 0.05% to about 5% such as 0.05% to about 0.5% by weight of the aqueous gel formulation; b) water; c) diethylene glycol monoethyl ether; and d) a gel-forming agent.

[37] The aqueous gel formulation of [36], wherein the acyclovir is in an amount of about 0.1% to about 0.3%, such as about 0.1%, about 0.15%, about 0.2%, about 0.25%, or about 0.3%, or any range between the recited values, such as about 0.15-0.25%, by weight of the aqueous gel formulation.

[38] The aqueous gel formulation of [36] or [37], further comprising a low molecular weight polyethylene glycol.

[39] The aqueous gel formulation of [38], wherein the low molecular weight polyethylene glycol has an average molecular weight less than 700, such as PEG 400.

[40] The aqueous gel formulation of [38] or [39], wherein the weight ratio of diethylene glycol monoethyl ether to the low molecular weight polyethylene glycol (e.g., PEG 400) ranges from about 20:1 to about 1:5.

[41] The aqueous gel formulation of any one of [38]-[40], wherein the weight ratio of diethylene glycol monoethyl ether to the low molecular weight polyethylene glycol (e.g., PEG 400) ranges from about 10:1 to about 2:1, such as about 6:1, about 5:1, about 4:1, about 3:1, about 2:1, or any ranges in between the recited values.

[42] The aqueous gel formulation of any one of [36]-[41], wherein the weight ratio of water to diethylene glycol monoethyl ether ranges from about 5:1 to about 1:5, such as about 1:1, about 1:1.5, about 1:2, about 1:3, or any ranges between the recited values.

[43] The aqueous gel formulation of any one of [36]-[42], further comprising propylene glycol.

[44] The aqueous gel formulation of any one of [36]-[42], which is free of or substantially free of propylene glycol.

[45] The aqueous gel formulation of any one of [36]-[44], comprising by weight of the aqueous gel formulation, water in an amount of about 25-65%, diethylene glycol monoethyl ether in an amount of about 25-70%, and PEG 400 in an amount of about 0-20%.

[46] The aqueous gel formulation of any one of [36]-[45], comprising by weight of the aqueous gel formulation, water in an amount of about 30-50%, diethylene glycol monoethyl ether in an amount of about 35-65%, and PEG 400 in an amount of about 5-15%.

[47] The aqueous gel formulation of any one of [36]-[46], wherein the gel-forming agent is a crosslinked polyacrylic acid (e.g., a crosslinked polyacrylic acid with allyl sucrose or allyl pentaerythritol such as Carbopol® 980).

[48] The aqueous gel formulation of any one of [36]-[47], wherein the gel-forming agent is in an amount of about 0.1% to about 5% by weight of the aqueous gel formulation, such as about 0.1-2% or about 0.1-1%.

[49] The aqueous gel formulation of any one of [36]-[48], wherein the pH of the aqueous gel formulation is about 4 to 8, such as about 5 to 7, e.g., about 5.5-6.5 or 6-6.5.

[50] The aqueous gel formulation of any one of [36]-[49], wherein acyclovir is the only active ingredient.

[51] The aqueous gel formulation of any one of [36]-[50], further comprising an antioxidant or preservative.

[52] The aqueous gel formulation of [51], wherein the antioxidant or preservative is selected from butylated hydroxytoluene, phenoxyethanol, sodium metabisulfite, EDTA, ascorbic acid, and combinations thereof

[53] The aqueous gel formulation of any one of [36]-[52], which is substantially free of acyclovir in a solid form.

[54] A method of treating or preventing herpes labialis in a subject in need thereof comprising topically applying to the subject an effective amount of the aqueous gel formulation of any one of [36]-[53].

[55] A method of treating or preventing herpes viral infections of the skin or mucosa of a subject in need thereof comprising topically applying to the subject an effective amount of the aqueous gel formulation of any one of [36]-[53].

[56] A method of treating or preventing herpes zoster infections of the skin or mucosa of a subject in need thereof comprising topically applying to the subject an effective amount of the aqueous gel formulation of any one of [36]-[53].

[57] A method of treating or preventing herpes varicella infections of the skin or mucosa of a subject in need thereof comprising topically applying to the subject an effective amount of the aqueous gel formulation of any one of [36]-[53].

[58] A method of treating or preventing one or more diseases selected from genital herpes simplex, neonatal herpes simplex, cold sores, shingles, acute chickenpox (e.g., in immunocompromised patients), acute mucocutaneous HSV infections (e.g., in immunocompromised patients), herpes of the eye, and herpes simplex blepharitis, the method comprising topically applying to a subject in need thereof an effective amount of the aqueous gel formulation of any one of any one of [1]-[14] and [36]-[53], the emulsified gel formulation of any one of [15]-[30], or the non-aqueous gel formulation of [31].

It is to be understood that both the foregoing summary and the following detailed description are exemplary and explanatory only, and are not restrictive of the invention herein.

BRIEF DESCRIPTION OF THE DRAWINGS/FIGURES

FIG. 1 presents graphs showing mean cumulative amount of acyclovir permeated per unit area ($\mu g/cm^2$) across dermatomed human abdominal skin from three skin donors. Each time point represents the mean±SEM, n=3-5 per donor.

Figure 2:
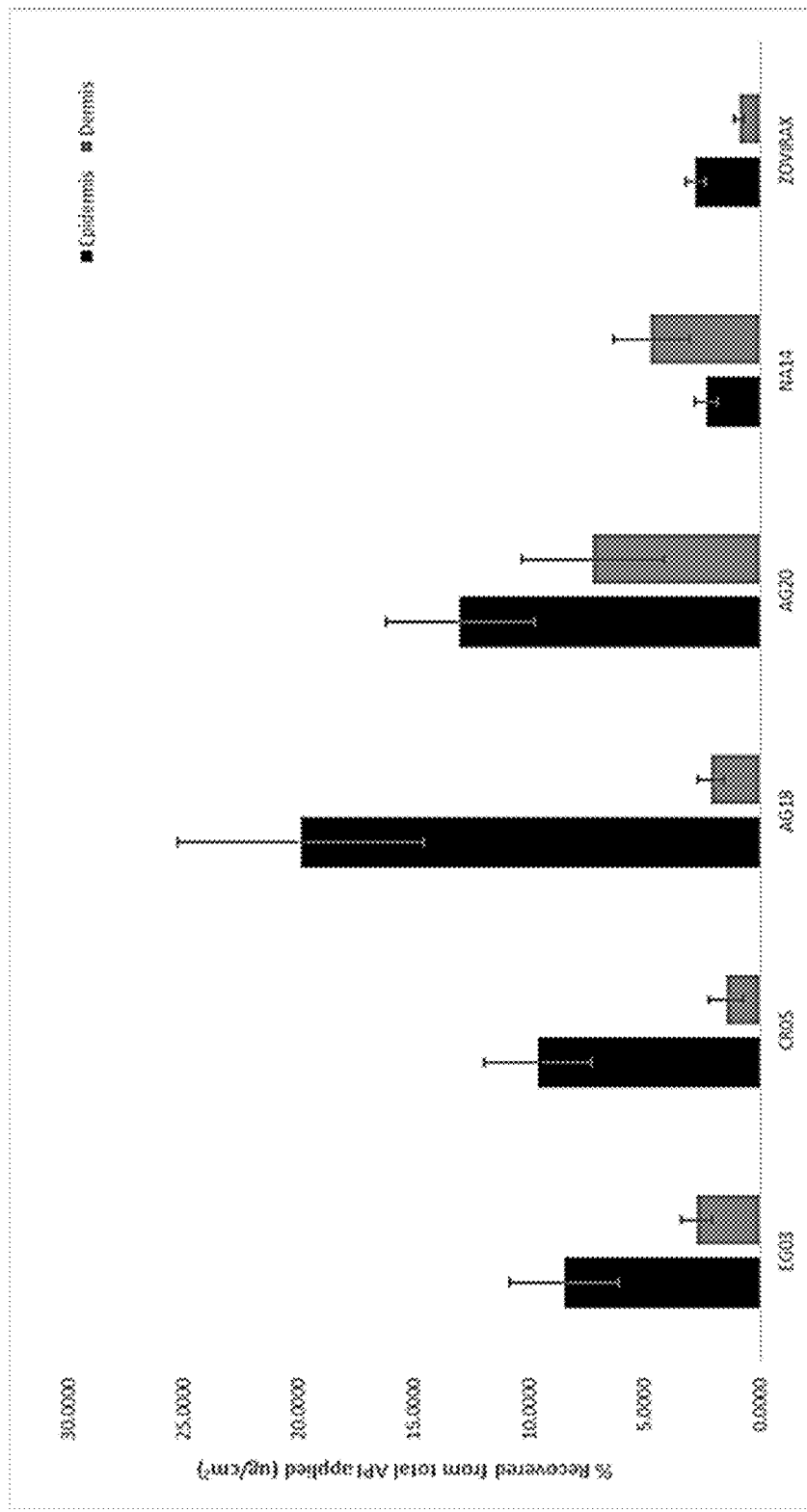

FIG. 2 presents bar graphs showing the amount of acyclovir recovered from the epidermis and dermis as a percentage of the applied dose at 28 hours following application of a range of active formulations and Zovirax® to dermatomed human abdominal skin from three skin donors.

Figure 3:
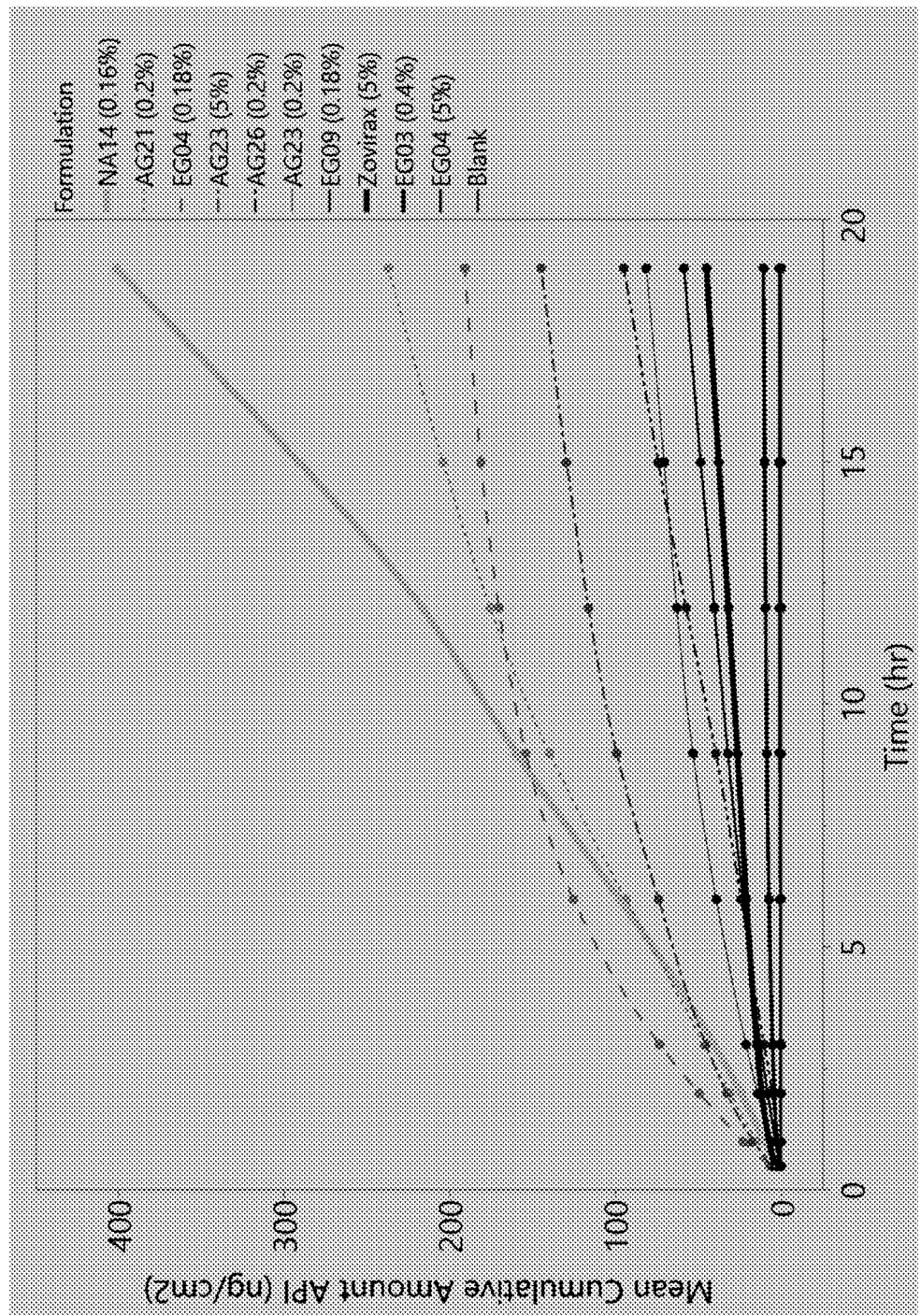

FIG. 3 presents a graph showing the mean cumulative amount ($ng/cm^2$) of acyclovir permeated through the 1 $cm^2$ skin dosing area into citrate/phosphate buffer pH 4.0 19 hours following application of 10 formulations. Single skin donor; n=4-7. For ease of viewing error bars removed. As can be seen from FIG. 3, at 19 hours, the cumulative amount of API delivered has the following ranking order: NA14>AG21>EG04>AG23-HC>AG26>AG23>EG09>Zovirax®>EG03>EG04-HC.

Figure 4:
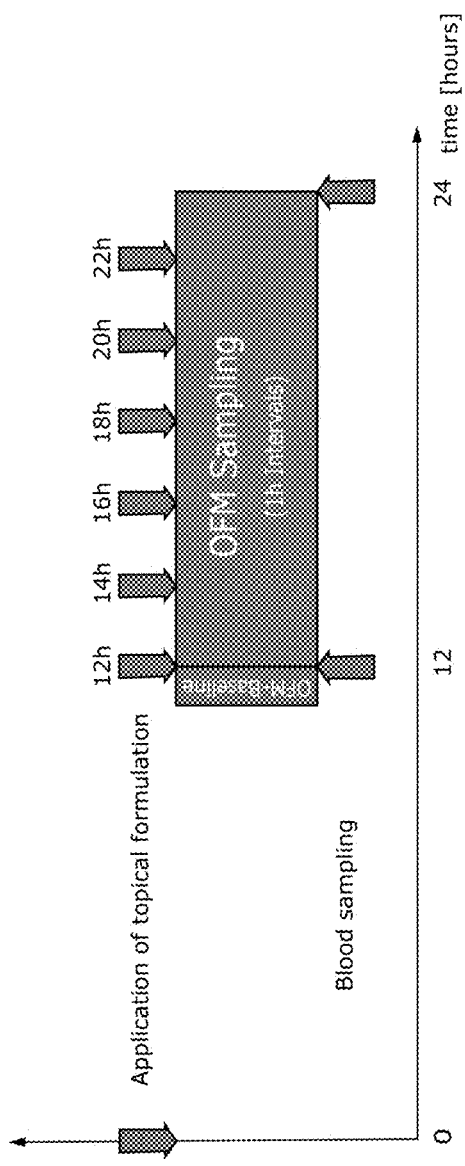

FIG. 4 shows the open flow micro perfusion/blood sampling schedule, dosing time of dose #2 (dosing at day 2) is defined as t=12 h.

Figure 5:
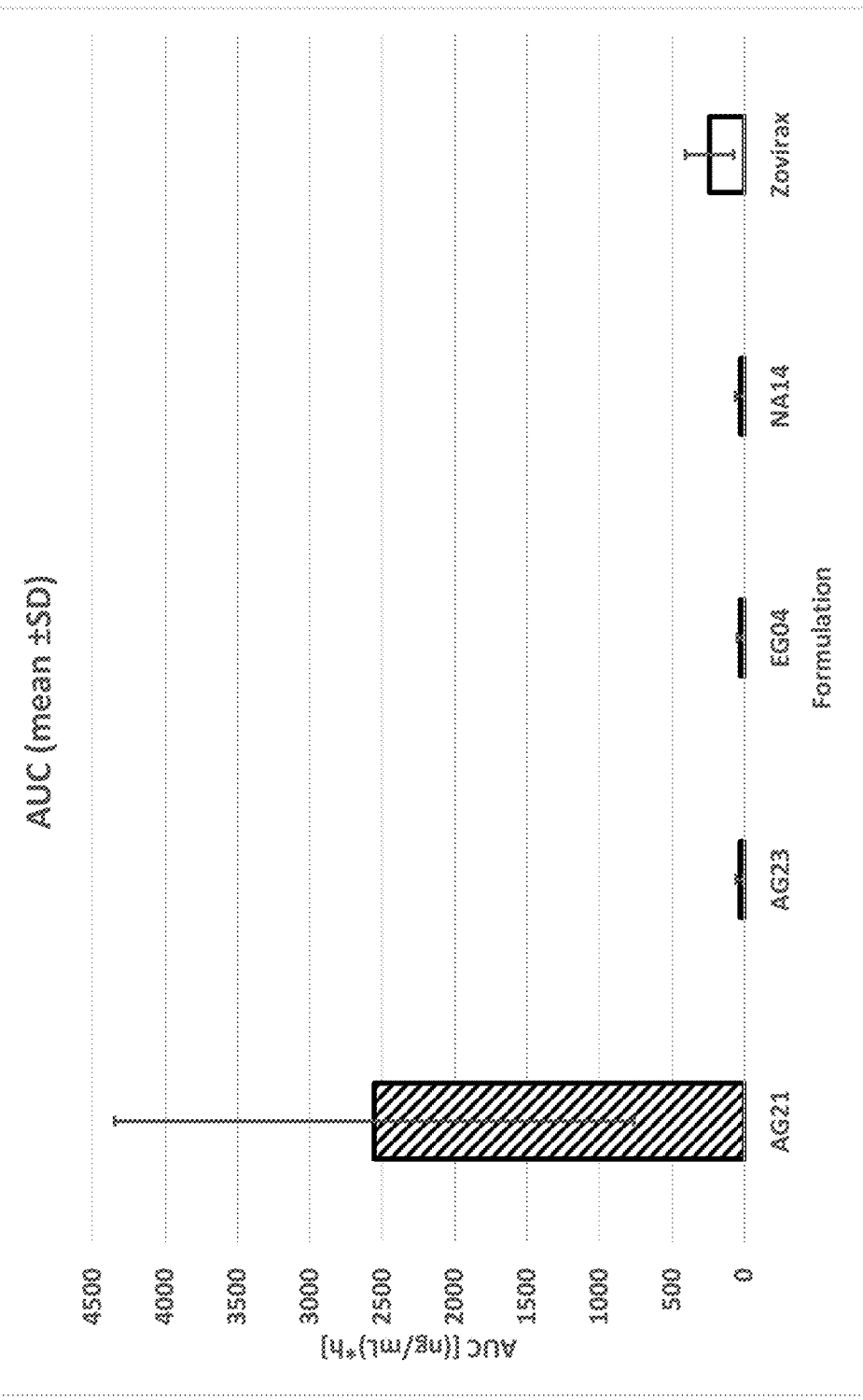

FIG. 5 presents bar graphs showing the area under the curve (AUC) of acyclovir from the dermal open flow micro perfusion studies for the five tested formulations (AG21, AG23, EG04, NA14, and Zovirax®). The data was expressed as mean±standard deviation (SD).

Figure 6:
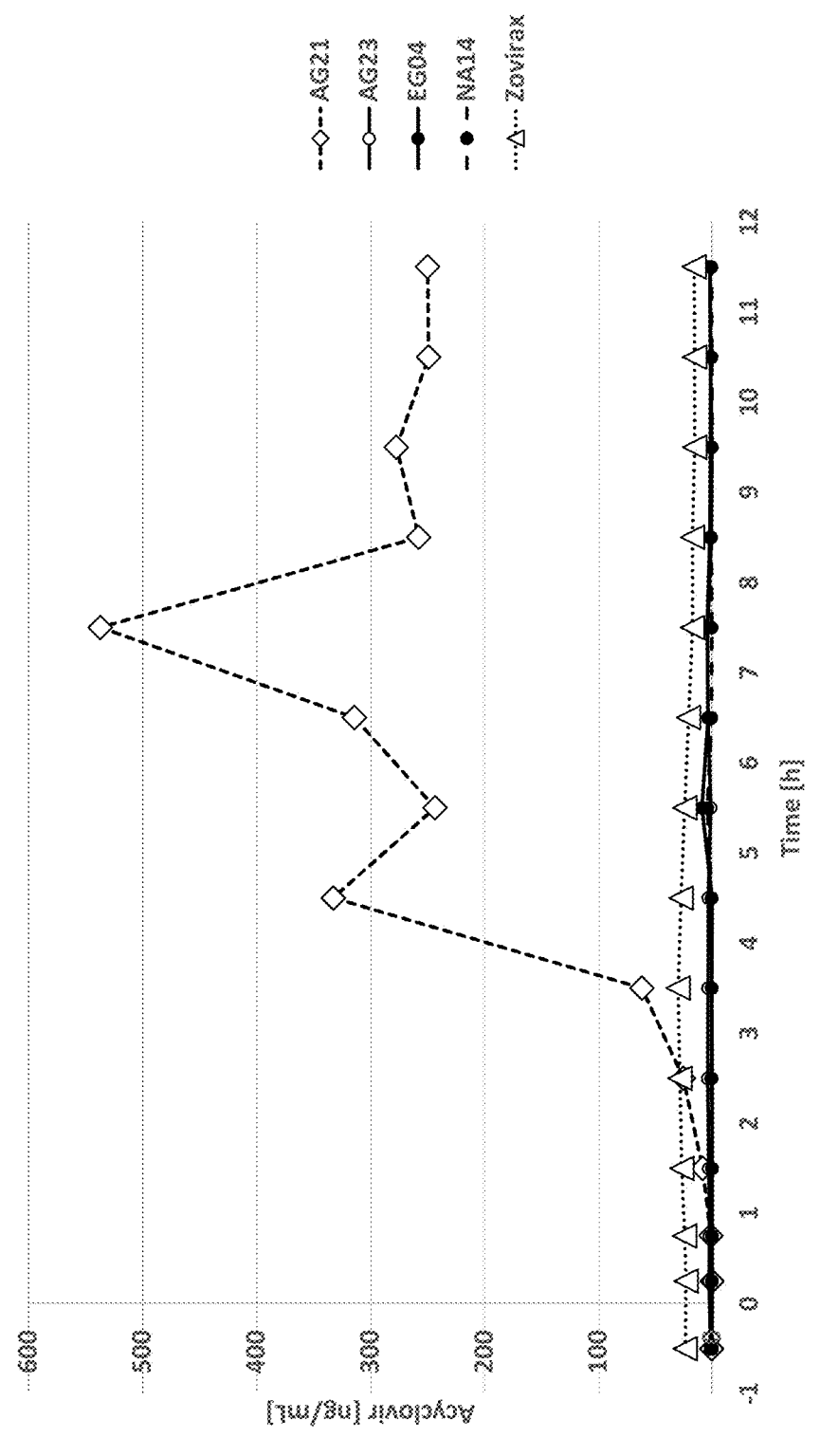

FIG. 6 presents a graph showing the mean acyclovir concentration in dermis vs. time profile from the dermal open flow micro perfusion studies for the five tested formulations (AG21, AG23, EG04, NA14, and Zovirax®).

DETAILED DESCRIPTION

The present disclosure is generally directed to an acyclovir gel formulation with a low concentration of acyclovir. The gel formulation of the present disclosure can be an aqueous gel formulation (non-emulsified gel), or an emulsified gel formulation. In some embodiments, the gel formulation can also be a non-aqueous gel formulation. In some embodiments, methods of using the acyclovir gel formulations of the present disclosure are also provided. For example, in some embodiments, the present disclosure is directed to methods of treating or preventing herpes labialis (cold sores), such as recurrent herpes labialis, in a subject in need thereof. As detailed herein, gel formulations of the present disclosure have several advantages over the marketed product Zovirax® Cream 5%, for example, with improved skin penetration and better patient compliance. As used herein, the marketed product Zovirax® Cream 5% refers to the U.S. FDA approved Zovirax® Cream 5% formulation (see e.g., Zovirax® Cream 5% Prescribing Information, rev. 2014). Although many of the embodiments herein are directed specifically to acyclovir, the novel gel system described herein is not so limited and can be used generally for antiviral purine nucleoside analogs. For example, for any of the embodiments described herein relating to gel formulation comprising acyclovir, alternative embodiments are also provided with the acyclovir replaced with another antiviral purine nucleoside analog, such as penciclovir, valacyclovir, etc. Further, the acyclovir herein is not limited to any specific form. For example, the acyclovir can be in the form of a free base, a pharmaceutically acceptable salt, a hydrate, solvate, or a polymorph, or a combination thereof. When in solution, those skilled in the art would understand that acyclovir can exist in both protonated and free form depending on the pH of the solution.

One characteristic of the gel formulations of the present disclosure is a significantly lowered acyclovir concentration compared to the marketed product Zovirax® Cream 5%. Without wishing to be bound by theories, it is believed that acyclovir can remain in solution at a lower concentration, which can enhance product consistency. As detailed herein, the gel formulations of the present disclosure have improved skin penetration compared to the marketed product Zovirax® Cream 5%. Thus, even though at a lower level of acyclovir, the gel formulation of the present disclosure delivers as much acyclovir into the skin as the marketed product Zovirax® Cream 5%. As shown in the Examples, some aqueous gel formulations with acyclovir in the range of 0.202% to 0.204% or emulsified gel formulations with acyclovir in the range of from 0.175% to 0.180% delivered as much acyclovir into the skin as did 5% cream or gel formulations, based upon the results of in vitro studies. The in vivo dermal open flow micro perfusion studies further suggest that certain aqueous gel formulations of the present disclosure can deliver a significant higher amount of acyclovir into the dermal interstitial fluids compared to that delivered by the marketed product Zovirax® Cream 5%.

The gel formulations of the present disclosure have several advantages over the marketed product Zovirax® Cream 5%. For example, in various embodiments, the gel formulations of the present disclosure can be stable and effective, and overcome some of the short comings of the Zovirax® Cream 5% (e.g., poor solubility of the drug in the commercial product (<0.5%), large particle range of acyclovir, and poor permeability). In some embodiments, the gel formulations of the present disclosure can also provide a more comfortable experience to a subject user due to its lowered drug concentration, and therefore enhance patient compliance.

Aqueous Gel Formulation

Some embodiments of the present disclosure are directed to aqueous gel formulations. As used herein, the aqueous gel formulation refers to a non-emulsified gel formulation. The aqueous gel formulations typically are formulated for topical use, which include acyclovir dissolved or partially suspended in an aqueous gel.

The acyclovir typically can be included in the aqueous gel formulations in an amount of less than 1% by weight. However, in some embodiments, the acyclovir can also be included at a higher concentration. For example, in some embodiments, the acyclovir can be included in the aqueous gel formulations in an amount of about 0.05% to about 5% (e.g., about 1-5%, about 2-5%, about 2-4%, etc.) by weight. In some embodiments, the acyclovir can be included in an amount of about 0.5% or less, about 0.4% or less, about 0.3% or less, about 0.2% or less, or about 0.1% or less by weight. In some embodiments, the acyclovir can be included in the aqueous gel formulation in an amount of about 0.02%, about 0.05%, about 0.1%, about 0.2%, about 0.3%, about 0.4%, or about 0.5% by weight, or any ranges between the recited values. For example, in one embodiment, the acyclovir can be present in an amount of about 0.05% to about 0.5% by weight. As used herein, unless obvious from context, the weight percentage is based on the final gel formulation. The weight percentage of acyclovir herein should be understood as calculated based on the free form.

The aqueous gel typically includes a solvent system and an effective amount of a gel-forming agent. The solvent system is generally selected to achieve a good solubility of acyclovir and/or an enhanced skin permeation of acyclovir, causing little to no skin irritation when applied.

The solvent system generally includes water and one or more water-miscible organic solvents. In some embodiments, the solvent system can comprise water in an amount of about 20% to about 80% by weight of the aqueous gel formulation; and one or more water-miscible organic solvents in an amount of about 15% to about 70% by weight of the aqueous gel formulation. In some embodiments, the solvent system can include water in an amount of about 20%, about 30%, about 40%, about 50%, about 60%, about 70%, about 80%, or any ranges between the recited values, by weight of the aqueous gel formulation. In some embodiments, the solvent system can include water in an amount of less than 50% (e.g., less than 40%, or less than 30%) by weight of the aqueous gel formulation. In some embodiments, the one or more water-miscible organic solvents can be in an amount of about 20%, about 30%, about 40%, about 50%, about 60%, about 70%, or any ranges between the recited values, by weight of the aqueous gel formulation. In some embodiments, the solvent system can include the one or more water-miscible organic solvents in an amount of more than 40% (e.g., more than 50%, or more than 60%) by weight of the aqueous gel formulation. The solvent system generally forms most of the weight of the aqueous gel formulation. In some embodiments, the solvent system forms about 70%, about 80%, about 90%, about 95%, or about 99%, or any ranges between the recited values, by weight of the aqueous gel formulation.

Various water-miscible organic solvents can be used for the aqueous gel formulations of the present disclosure. Non-limiting useful water-miscible organic solvents include propylene glycol, glycerol, Transcutol® (diethylene glycol monoethyl ether), dimethyl sulfoxide (DMSO), and a low molecular weight polyethylene glycol (PEG). For example, in some embodiments, the solvent system includes propylene glycol, e.g., in an amount of about 5% to about 30% (e.g., about 5%, about 10%, about 20%, about 30%, or any ranges between the recited values) by weight of the aqueous gel formulation. In some embodiments, the solvent system includes Transcutol®, e.g., in an amount of about 10% to about 60% (e.g., about 20%, about 30%, about 40%, about 50%, or any ranges between the recited values) by weight of the aqueous gel formulation. In some embodiments, the solvent system includes a low molecular weight polyethylene glycol (PEG), such as PEG 200-1000, such as PEG 200, PEG 400, PEG 450, PEG 500, PEG 600, etc., e.g., in an amount of about 5% to about 40% (e.g., about 10%, about 20%, about 30%, about 40%, or any ranges between the recited values) by weight of the aqueous gel formulation. In some embodiments, the solvent system includes more than one, such as two, three, or four, water-miscible organic solvents. In some embodiments, the solvent system includes at least two solvents selected from propylene glycol, Transcutol® and a low molecular weight PEG (e.g., PEG 400). In some embodiments, the solvent system includes a combination of propylene glycol, Transcutol® and a low molecular weight PEG (e.g., PEG 400). When two or more water-miscible organic solvents are included, the ratio of these water-miscible organic solvents can vary. For example, in a solvent system having a combination of propylene glycol, Transcutol®, and PEG 400, any one of the solvents can be in an amount of about 5-90% by weight of the total amount of the water-miscible organic solvents. In some embodiments, the solvent system can also be free or substantially free of a certain water-miscible organic solvent. For example, in some embodiments, the solvent system can be free or substantially free of ethanol. In some embodiments, the solvent system can be free or substantially free of isopropanol. In some embodiments, the solvent system can be free or substantially free of DMSO. In some embodiments, the solvent system can be free or substantially free of glycerol. In some embodiments, the solvent system can be free or substantially free of propylene glycol. A solvent system substantially free of a specified solvent as used herein refers to the solvent system containing less than 10% (e.g., less than 5%, less than 2%, or less than 1%, or undetectable amount (or alternatively referred to as "free of")) by weight of the specified solvent based on the total amount of the solvent system. The term "substantially free" as used in other context should be understood similarly.

The gel-forming agent can be any of those known in the art suitable for topical use. For example, suitable gel-forming agents can include polysaccharides, such as, cellulose derivatives, e.g., hydroxypropyl cellulose, hydroxypropyl methylcellulose, hydroxyethyl methylcellulose and carboxymethylcellulose and salts thereof; acrylic polymers such as polyacrylic acids and polymethacrylates, e.g. carbopol such as carbopol homopolymer, e.g., a crosslinked polyacrylic acid with allyl sucrose or allyl pentaerythritol, poly(hydroxyethyl methacrylate), poly(methoxyethyl methacrylate) and poly(methoxyethoxyethyl methacrylate); proteins such as gelatin; high average molecular weight polyhydroxy compounds such as polyvinyl alcohols; high average molecular weight polyalkylene glycols such as polyethylene glycols, optionally cross-linked, with an average molecular weight from about 20,000 to about 4,000,000; and polyvinylpyrrolidone with an average molecular weight in the range from 10,000 to 700,000. Typically, the gel-forming agent is included in the aqueous gel formulation in a gel-forming effective amount. In some embodiments, the gel forming agent is in an amount of about 0.1% to about 5% (e.g., about 0.1%, about 0.5%, about 1%, about 2%, about 5%, or any ranges between the recited values) by weight of the aqueous gel formulation. In some embodiments, the gel forming agent can be a crosslinked polyacrylic acid, such as a crosslinked polyacrylic acid with allyl sucrose or allyl pentaerythritol, such as Carbopol® 980.

The pH of the aqueous gel formulation is typically from about 4 to about 8. In some embodiments, the pH of the aqueous gel formulation can be from about 5 to about 7, for example, about 6 to about 6.5.

In some embodiments, acyclovir can be included in the aqueous gel formulation as the only active ingredient. However, in some embodiments, acyclovir can also be included together with an additional active ingredient in the aqueous gel formulation. Such additional active ingredient can be, for example, another antiviral agent, or an agent that can supplement the action of acyclovir and/or reduce a side effect of acyclovir. Useful additional active ingredients include those suitable for topical use. In some embodiments, such additional active ingredient can be dissolved or partially suspended in the aqueous gel formulation. For example, in some embodiments, the aqueous gel formulation can include one or more additional active agents selected from anti-allergic medications, glucocorticoids, corticosteroids, anti-inflammatory agents, pain relievers, local anesthetics, and combinations thereof. In some embodiments, the aqueous gel formulation can include one or more additional active agents selected from selected from 2-deoxy-D-glucose, oxatamide, betamethasone, valerate, dexamethasone, triamcinolone acetonide, clobetasone butyrate, hydrocortisone, triamcinolone, flurbiprofen, ketorolace, lidocaine, benzocaine, articaine, chlorprocaine, cocaine, dydloninem, proparacaine, mepivacaine, prilocalne, procaine, tetracaine, pramoxin, and combinations thereof. In some embodiments, the aqueous gel formulation can include a corticosteroid, such as a glucocorticoid, for example, hydrocortisone.

In some embodiments, the aqueous gel formulation can also include an antioxidant or preservative. For example, in some embodiments, the aqueous gel formulation can include an antioxidant or preservative selected from butylated hydroxytoluene, phenoxyethanol, sodium metabisulfite, EDTA, ascorbic acid, and combinations thereof. In some embodiments, the aqueous gel formulation comprises phenoxyethanol. When present, the antioxidant or preservative is typically included in an amount of about 0.05% to about 5% (e.g., about 0.1%, about 0.5%, about 1%, about 2%, about 5%, or any ranges between the recited values) by weight of the aqueous gel formulation.

Other suitable excipients useful in the preparation of the aqueous gel formulations include humectants, sweeteners, flavorings, penetration enhancers, plasticizers, anti-irritants, emollients, surfactants, drug release modifiers, etc. These excipients are within the knowledge of those skilled in the art, and can be found, for example, in the Handbook of Pharmaceutical Excipients ($7^{th}$ Ed. 2012). In some embodiments, the aqueous gel formulations can also be free of or substantially free of an anionic surfactant, such as a fatty acid salt or a fatty sulfate salt.

Aqueous Gel Formulation Comprising Transcutol

It was discovered that the use of Transcutol (diethylene glycol monoethyl ether) in the aqueous gel formulations herein is beneficial, for example, for achieving a desired acyclovir permeation profile. For example, as shown in the Examples section herein, aqueous gel AG21, which has almost 50% Transcutol, achieved much higher delivery of acyclovir to the dermis interstitial fluids than did Zovirax® cream 5% when measured by dermal open flow micro perfusion in vivo.

In some embodiments, the present disclosure provides an aqueous gel formulation comprising: a) acyclovir in an amount of about 0.05% to about 0.5% by weight of the aqueous gel formulation; b) water; c) diethylene glycol monoethyl ether; and d) a gel-forming agent. However, in some embodiments, the acyclovir can also be included at a higher concentration. For example, in some embodiments, the present disclosure provides an aqueous gel formulation comprising: a) acyclovir in an amount of about 0.05% to about 5% (e.g., about 1-5%, about 2-5%, about 2-4%, etc.) by weight of the aqueous gel formulation; b) water; c) diethylene glycol monoethyl ether; and d) a gel-forming agent.

In some embodiments, the acyclovir can be present in an amount of about 0.1% to about 0.3%, such as about 0.1%, about 0.15%, about 0.2%, about 0.25%, or about 0.3%, or any range between the recited values, such as about 0.15-0.25%, by weight of the aqueous gel formulation. Typically, the acyclovir can be included in the aqueous gel formulation in an amount such that it can be dissolved in the aqueous gel formulation. In other words, in a typical embodiment, the aqueous gel formulation is free of or substantially free of acyclovir in a solid form, such as with no visible (macroscopically or microscopically) suspended acyclovir particles or crystals. In some embodiments, the aqueous gel formulation can include acyclovir in an amount not more than the maximum solubility of acyclovir in the solvent system of the aqueous gel formulation. In some embodiments, the aqueous gel formulation can include acyclovir in an amount substantially equal to the maximum solubility of acyclovir in the solvent system of the aqueous gel formulation.

The aqueous gel formulation typically also includes a low molecular weight polyethylene glycol. However, in some embodiments, the aqueous gel formulation can also be free of such low molecular weight polyethylene glycol. When present, the low molecular weight polyethylene glycol is typically chosen from those that are liquids at room temperature. In some embodiments, the low molecular weight polyethylene glycol has an average molecular weight less than 1000, for example, less than 700, such as PEG 400.

Various amounts of low molecular weight polyethylene glycol can be suitably included in the aqueous gel formulation herein. For example, in some embodiments, the aqueous gel formulation can have a weight ratio of diethylene glycol monoethyl ether to the low molecular weight polyethylene glycol (e.g., PEG 400) ranging from about 20:1 to about 1:5, for example, about 20:1, about 15:1, about 10:1, about 5:1, about 1:1, about 1:2, or about 1:5, or any ranges in between the recited values. In some preferred embodiments, the aqueous gel formulation can have a weight ratio of diethylene glycol monoethyl ether to the low molecular weight polyethylene glycol (e.g., PEG 400) ranging from about 10:1 to about 2:1, such as about 6:1, about 5:1, about 4:1, about 3:1, about 2:1, or any ranges in between the recited values.

Water is typically included in the aqueous gel formulation at a weight ratio to diethylene glycol monoethyl ether ranging from about 10:1 to about 1:10, more typically, from about 5:1 to about 1:5, such as about 1:1, about 1:1.5, about 1:2, about 1:3, or any ranges between the recited values.

In some embodiments, the aqueous gel formulation comprises a solvent system that comprises, consists essentially of, or consists of water, diethylene glycol monoethyl ether, and the low molecular weight polyethylene glycol (e.g., PEG 400). In some embodiments, the aqueous gel formulation can also include one or more additional solvents, such as the water-miscible organic solvents described herein. For example, in some embodiments, the aqueous gel formulation can also include propylene glycol. However, in some embodiments, the aqueous gel formulation can also be free of propylene glycol. As described herein, it was unexpectedly found that between the two aqueous gel formulations AG21 and AG23, much higher levels of acyclovir permeated into the dermal interstitial fluids from AG21 when both were tested in pig dermal open flow micro-perfusion studies. Without wishing to be bound by theories, it is believed that this is due to the better permeation-enhancing effect of diethylene glycol monoethyl ether compared to that of propylene glycol, as the main difference between AG21 and AG23 is that the majority of about 20% by weight of propylene glycol in AG23 is replaced with diethylene glycol monoethyl ether in AG21.

In some embodiments, the aqueous gel formulation comprises water, diethylene glycol monoethyl ether, and PEG 400. In some embodiments, the aqueous gel formulation comprises by weight of the aqueous gel formulation, water in an amount of about 25-65% (e.g., about 25%, about 30%, about 35%, about 40%, about 45%, about 50%, about 60%, about 65%, or any ranges in between the recited values such as about 25-60%, about 30-60%, about 30-50%, etc.), diethylene glycol monoethyl ether in an amount of about 25-70% (e.g., about 25%, about 30%, about 35%, about 40%, about 45%, about 50%, about 55%, about 60%, about 65%, about 70%, or any ranges in between the recited values such as about 25-60%, about 35-70%, about 30-50%, etc.), and PEG 400 in an amount of about 0-20% (e.g., about 1%, about 5%, about 10%, about 15%, about 20%, or any ranges in between the recited values such as about 5-20%, about 5-15%, about 10-20%, etc.). In some embodiments, the weight ratio of diethylene glycol monoethyl ether to PEG 400 ranges from about 20:1 to about 1:5, for example, about 20:1, about 15:1, about 10:1, about 5:1, about 1:1, about 1:2, or about 1:5, or any ranges in between the recited values. In some preferred embodiments, the weight ratio of diethylene glycol monoethyl ether to the PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 2:1 to about 1:2, such as about 2:1, about 1.5:1, about 1:1, about 1:1.5, about 1:2, or any ranges between the recited values.

In some specific embodiments, the aqueous gel formulation comprises: a) acyclovir in an amount of about 0.1% to about 0.3% (e.g., about 0.15%, about 0.2%, about 0.25%, or about 0.15-0.25%) by weight of the aqueous gel formulation; b) water in an amount of about 30-50% (e.g., about 30%, about 35%, about 40%, about 45%, about 50%, or any ranges in between the recited values) by weight of the aqueous gel formulation; c) diethylene glycol monoethyl ether in an amount of about 35-65% (e.g., about 35%, about 40%, about 45%, about 50%, about 55%, about 60%, about 65%, or any ranges in between the recited values such as about 45-55%, about 40-60%, about 35-55%, etc.) by weight of the aqueous gel formulation; d) PEG 400 in an amount of about 5-15% (e.g., about 5%, about 10%, about 15%, or any ranges in between the recited values) by weight of the aqueous gel formulation; and e) a gel forming agent. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.4:1 to about 1:2, such as about 1.2:1, about 1:1, about 1:1.5, about 1:2, or any ranges between the recited values. Suitable pH and other optionally ingredients include any of those described herein in any combination.

Typically, the gel-forming agent is included in the aqueous gel formulation in a gel-forming effective amount. In some embodiments, the gel forming agent is in an amount of about 0.1% to about 5% (e.g., about 0.1%, about 0.5%, about 1%, about 2%, about 5%, or any ranges between the recited values such as about 0.1-2% or about 0.1-1%) by weight of the aqueous gel formulation. In some embodiments, the gel forming agent can be a crosslinked polyacrylic acid, such as a crosslinked polyacrylic acid with allyl sucrose or allyl pentaerythritol, such as Carbopol® 980. Other suitable gel forming agent include any of those described herein.

In some specific embodiments, the aqueous gel formulation comprises: a) acyclovir in an amount of about 0.1% to about 0.3% (e.g., about 0.15%, about 0.2%, about 0.25%, or about 0.15-0.25%) by weight of the aqueous gel formulation; b) water in an amount of about 30-50% (e.g., described herein) by weight of the aqueous gel formulation; c) diethylene glycol monoethyl ether in an amount of about 35-65% (e.g., described herein) by weight of the aqueous gel formulation; d) PEG 400 in an amount of about 5-15% (e.g., described herein) by weight of the aqueous gel formulation; and e) a crosslinked polyacrylic acid, such as a crosslinked polyacrylic acid with allyl sucrose or allyl pentaerythritol, such as Carbopol® 980, in an amount of about 0.1% to about 1% (e.g., about 0.1%, about 0.5%, about 1%, or any ranges between the recited values) by weight of the aqueous gel formulation. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.4:1 to about 1:2, such as about 1.2:1, about 1:1, about 1:1.5, about 1:2, or any ranges between the recited values. Suitable pH and other optionally ingredients include any of those described herein in any combination.

The pH of the aqueous gel formulation typically ranges from about 4 to about 8. In some embodiments, the pH of the aqueous gel formulation can be from about 5 to about 7, for example, about 6 to about 6.5.

In some embodiments, acyclovir can be included in the aqueous gel formulation as the only active ingredient. However, in some embodiments, acyclovir can also be included together with an additional active ingredient in the aqueous gel formulation, e.g., as described herein. Such additional active ingredient can be, for example, another antiviral agent, or an agent that can supplement the action of acyclovir and/or reduce a side effect of acyclovir. Useful additional active ingredients include those suitable for topical use. In some embodiments, such additional active ingredient can be dissolved or partially suspended in the aqueous gel formulation.

In some embodiments, the aqueous gel formulation can also include an antioxidant or preservative. For example, in some embodiments, the aqueous gel formulation can include an antioxidant or preservative selected from butylated hydroxytoluene, phenoxyethanol, sodium metabisulfite, EDTA, ascorbic acid, and combinations thereof. In some embodiments, the aqueous gel formulation comprises phenoxyethanol. When present, the antioxidant or preservative is typically included in an amount of about 0.05% to about 5% (e.g., about 0.1%, about 0.5%, about 1%, about 2%, about 5%, or any ranges between the recited values) by weight of the aqueous gel formulation.

Other suitable excipients useful in the preparation of the aqueous gel formulations include humectants, sweeteners, flavorings, penetration enhancers, plasticizers, anti-irritants, emollients, surfactants, drug release modifiers, etc. These excipients are within the knowledge of those skilled in the art, and can be found, for example, in the Handbook of Pharmaceutical Excipients (7$^{th}$ Ed. 2012). In some embodiments, the aqueous gel formulations can also be free of or substantially free of an anionic surfactant, such as a fatty acid salt or a fatty sulfate salt.

In some specific embodiments, the aqueous gel formulation comprises: a) acyclovir in an amount of about 0.1% to about 0.3% (e.g., about 0.15%, about 0.2%, about 0.25%, or about 0.15-0.25%) by weight of the aqueous gel formulation; b) water in an amount of about 30-50% (e.g., described herein) by weight of the aqueous gel formulation; c) diethylene glycol monoethyl ether in an amount of about 35-65% (e.g., described herein) by weight of the aqueous gel formulation; d) PEG 400 in an amount of about 5-15% (e.g., described herein) by weight of the aqueous gel formulation; e) a crosslinked polyacrylic acid, such as a crosslinked polyacrylic acid with allyl sucrose or allyl pentaerythritol, such as Carbopol® 980, in an amount of about 0.1% to about 1% (e.g., described herein) by weight of the aqueous gel formulation; and f) phenoxyethanol in an amount of about 0.05% to about 2% (e.g., about 0.1%, about 0.5%, about 1%, about 2%, or any ranges between the recited values) by weight of the aqueous gel formulation. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.4:1 to about 1:2, such as about 1.2:1, about 1:1, about 1:1.5, about 1:2, or any ranges between the recited values. In some embodiments, the aqueous gel formulations is free of or substantially free of an anionic surfactant, such as a fatty acid salt or a fatty sulfate salt. Suitable pH and other optionally ingredients include those described herein in any combination.

In some specific embodiments, the aqueous gel formulation comprises the following ingredients (by weight of the aqueous gel formulation): acyclovir (about 0.2%), water (about 39.3%), PEG 400 (about 9.1%), phenoxyethanol (about 1%), Transcutol, i.e., diethylene glycol monoethyl ether (about 49.9%), Carbopol® 980 (about 0.5%), optional pH adjusting agent, with the total amount being 100%. The pH is typically adjusted to about 5-7, such as about 5.5-6.5 or 6-6.5.

In some specific embodiments, the aqueous gel formulation comprises the following ingredients (by weight of the aqueous gel formulation): acyclovir (about 0.2%), water (about 39.5%), PEG 400 (about 11.7%), phenoxyethanol (about 1%), Transcutol, i.e., diethylene glycol monoethyl ether (about 28.2%), propylene glycol (about 19.1%), Carbopol® 980 (about 0.35%), optional pH adjusting agent, with the total amount being 100%. The pH is typically adjusted to about 5-7, such as about 5.5-6.5 or 6-6.5.

Method of Preparing Aqueous Gel Formulation

In some embodiments, the present disclosure also provides a method of preparing an aqueous gel formulation described herein. The aqueous gel formulation described herein (e.g., those including Transcutol) can be readily prepared by those skilled in the art in view of the present disclosure. In one typical embodiment, the method comprises 1) mixing and optionally dissolving acyclovir with other ingredients of the aqueous gel formulation to form an acyclovir solution or suspension; 2) adding a gel-forming agent to the acyclovir solution or suspension to form an aqueous gel; and 3) optionally adjusting the pH of the aqueous gel.

For example, in some embodiments, the method is for preparing the aqueous gel formulation described herein comprising: a) acyclovir in an amount of about 0.1% to about 0.3% (e.g., about 0.15%, about 0.2%, about 0.25%, or about 0.15-0.25%) by weight of the aqueous gel formulation; b) water in an amount of about 30-50% (e.g., described herein) by weight of the aqueous gel formulation; c) diethylene glycol monoethyl ether in an amount of about 35-65% (e.g., described herein) by weight of the aqueous gel formulation; d) PEG 400 in an amount of about 5-15% (e.g., described herein) by weight of the aqueous gel formulation; e) a gel forming agent, such as a crosslinked polyacrylic acid, such as a crosslinked polyacrylic acid with allyl sucrose or allyl pentaerythritol, e.g., Carbopol® 980, in an amount of about 0.1% to about 1% (e.g., described herein) by weight of the aqueous gel formulation; and optionally f) an antioxidant/preservative, e.g., phenoxyethanol, in an amount of about 0.05% to about 2% (e.g., about 0.1%, about 0.5%, about 1%, about 2%, or any ranges between the recited values) by weight of the aqueous gel formulation, the method comprises: 1) dissolving the acyclovir in a mixture comprising water, diethylene glycol monoethyl ether, PEG 400, and the optional antioxidant/preservative to form an acyclovir solution; 2) adding the gel forming agent to the acyclovir solution to form an aqueous gel; and 3) optionally adjusting the pH of the aqueous gel. In some embodiments, the pH is adjusted to about 4 to about 8, e.g., about 5-7 or about 5.5-6.5 or 6-6.5, for example, with an alkali hydroxide base such as NaOH. Typically, after the pH is adjusted to a desired range, a second addition of water can be conducted and the mixture can be mixed to form a homogenous mixture. The appropriate amount of each ingredient varies according to the final aqueous gel formulation to be prepared. Typically, all ingredients are mixed with the acyclovir to form the acyclovir solution in step 1) or added to the acyclovir solution of step 1), except a portion of the water, optional pH adjusting agent, and the gel forming agent. A representative procedure is described in the Examples section.

It should be noted that the aqueous gel formulation and acyclovir solution prepared by the methods herein are also novel compositions of the present disclosure.

Emulsified Gel Formulation

The water containing gel formulations herein can be a non-emulsified gel (referred to herein as "aqueous gel formulation") or an emulsified gel. In a non-emulsified gel, the formulation typically does not include any significant amount of excipients insoluble in water or the solvent system. In such formulations, no emulsifier is necessary. In an emulsified gel, the formulation typically includes an excipient that forms an emulsion with water or the solvent system, such as a fatty ester emollient, and an emulsifier in an amount sufficient to create a stable emulsion. The emulsion can be an oil-in-water emulsion or a water-in-oil emulsion.

Some embodiments of the present disclosure are directed to emulsified gel formulations. The emulsified gel formulations typically are formulated for topical use, which include acyclovir dissolved or partially suspended in an emulsified gel. Like the aqueous gel formulations described herein, the acyclovir typically can be included in the emulsified gel formulations in an amount of less than 1% by weight. However, in some embodiments, the acyclovir can also be included at a higher concentration. For example, in some embodiments, the acyclovir can be included in the emulsified gel formulations in an amount of about 0.05% to about 5% (e.g., about 1-5%, about 2-5%, about 2-4%, etc.) by weight. In some embodiments, the acyclovir can be included in an amount of about 0.5% or less, about 0.4% or less, about 0.3% or less, about 0.2% or less, or about 0.1% or less by weight. In some embodiments, the acyclovir can be included in the emulsified gel formulation in an amount of about 0.02%, about 0.05%, about 0.1%, about 0.2%, about 0.3%, about 0.4%, or about 0.5% by weight, or any ranges between the recited values. For example, in one embodiment, the acyclovir can be present in an amount of about 0.05% to about 0.5% by weight.

The emulsified gel typically includes a solvent system, an oil, an emulsifier, and an effective amount of a gel-forming agent. The solvent system and oil are generally selected to achieve a good solubility of acyclovir and/or an enhanced skin permeation of acyclovir, causing little to no skin irritation when applied.

The solvent system generally includes water and one or more water-miscible organic solvents. In some embodiments, the solvent system can comprise water in an amount of about 20% to about 80% by weight of the emulsified gel formulation; and one or more water-miscible organic solvents in an amount of about 15% to about 70% by weight of the emulsified gel formulation. In some embodiments, the solvent system can include water in an amount of about 20%, about 30%, about 40%, about 50%, about 60%, about 70%, about 80%, or any ranges between the recited values, by weight of the emulsified gel formulation. In some embodiments, the solvent system can include water in an amount of less than 50% (e.g., less than 40%, or less than 30%) by weight of the emulsified gel formulation. In some embodiments, the one or more water-miscible organic solvents can be in an amount of about 20%, about 30%, about 40%, about 50%, about 60%, about 70%, or any ranges between the recited values, by weight of the emulsified gel formulation. In some embodiments, the solvent system can include the one or more water-miscible organic solvents in an amount of more than 40% (e.g., more than 50%, or more than 60%) by weight of the emulsified gel formulation. The solvent system generally forms most of the weight of the emulsified gel formulation. In some embodiments, the solvent system forms about 70%, about 80%, about 90%, or about 95%, or any ranges between the recited values, by weight of the emulsified gel formulation.

Various water-miscible organic solvents can be used for the emulsified gel formulations of the present disclosure. Non-limiting useful water-miscible organic solvents include propylene glycol, glycerol, Transcutol® (diethylene glycol monoethyl ether), dimethyl sulfoxide (DMSO), and a low molecular weight polyethylene glycol (PEG). For example, in some embodiments, the solvent system includes propylene glycol, e.g., in an amount of about 5% to about 30% (e.g., about 5%, about 10%, about 20%, about 30%, or any ranges between the recited values) by weight of the emulsified gel formulation. In some embodiments, the solvent system includes Transcutol®, e.g., in an amount of about 10% to about 60% (e.g., about 20%, about 30%, about 40%, about 50%, or any ranges between the recited values) by weight of the emulsified gel formulation. In some embodiments, the solvent system includes a low molecular weight polyethylene glycol (PEG), such as PEG 200-1000, such as PEG 200, PEG 400, PEG 450, PEG 500, PEG 600, etc., e.g., in an amount of about 5% to about 40% (e.g., about 10%, about 20%, about 30%, about 40%, or any ranges between the recited values) by weight of the emulsified gel formulation. In some embodiments, the solvent system includes more than one, such as two, three, or four, water-miscible organic solvents. In some embodiments, the solvent system includes at least two solvents selected from propylene glycol, Transcutol® and a low molecular weight PEG (e.g., PEG 400). In some embodiments, the solvent system includes a combination of propylene glycol, Transcutol® and a low molecular weight PEG (e.g., PEG 400). When two or more water-miscible organic solvents are included, the ratio of these water-miscible organic solvents can vary. For example, in a solvent system having a combination of propylene glycol, Transcutol®, and PEG 400, any one of the solvents can be in an amount of about 5-90% by weight of the total amount of the water-miscible organic solvents. In some embodiments, the solvent system can also be free or substantially free of a certain water-miscible organic solvent. For example, in some embodiments, the solvent system can be free or substantially free of ethanol. In some embodiments, the solvent system can be free or substantially free of isopropanol. In some embodiments, the solvent system can be free or substantially free of DMSO. In some embodiments, the solvent system can be free or substantially free of glycerol. In some embodiments, the solvent system can be free or substantially free of propylene glycol.

The gel-forming agent can be any of those known in the art suitable for topical use. Non-limiting suitable gel-forming agents include those described herein. Typically, the gel-forming agent is included in the emulsified gel formulation in a gel-forming effective amount. In some embodiments, the gel forming agent is in an amount of about 0.1% to about 5% (e.g., about 0.1%, about 0.5%, about 1%, about 2%, about 5%, or any ranges between the recited values) by weight of the aqueous gel formulation. In some embodiments, the gel forming agent can be a crosslinked polyacrylic acid, such as a crosslinked polyacrylic acid with allyl sucrose or allyl pentaerythritol, such as Carbopol® 980.

In some embodiments, the oil can include an emollient. In some embodiments, the emollient can include a fatty ester, a triglyceride of caprylic and/or capric acid or a mixed ester of palm oil or coconut oil, such as Crodamol™ GTCC. For example, in some embodiments, the emollient can include medium chain triglycerides of caprylic (C8) and capric (C10) acids, e.g., derived from palm oil or coconut oil. In some embodiments, the emollient forms an emulsion with water or the solvent system. In some embodiments, the oil, e.g., emollient, can be included in an amount of about 1% to about 20% (e.g., about 5%, about 10%, about 15%, about 20%, or any ranges between the recited values) by weight of the emulsified gel formulation.

Various emulsifiers can be suitable for use herein. In some embodiments, the emulsifier can also be a gel-forming agent, for example, the emulsifier can comprise an acrylamide and acryloyldimethyl taurate copolymer and a non-ionic surfactant. In some embodiments, the emulsifier comprises an acrylamide and sodium acryloyldimethyl taurate copolymer dispersed in isohexadecane and a non-ionic surfactant (e.g., polysorbate, such as polysorbate 80). An example of such dual functional emulsifier is the commercially available Sepineo™ P 600. In some embodiments, the emulsifier is different from the gel-forming agent. Other emulsifiers can be selected by those skilled in the art in light of this disclosure. When present, the emulsifier is typically included in an amount of about 1% to about 10% (e.g., about 1%, about 5%, about 10%, or any ranges between the recited values) by weight of the emulsified gel formulation.

The pH of the emulsified gel formulation is typically from about 4 to about 8. In some embodiments, the pH of the emulsified gel formulation can be from about 5 to about 7, for example, about 6 to about 6.5.

In some embodiments, acyclovir can be included in the emulsified gel formulation as the only active ingredient. However, in some embodiments, acyclovir can also be included together with an additional active ingredient in the emulsified gel formulation. Such additional active ingredient can be, for example, another antiviral agent, or an agent that can supplement the action of acyclovir and/or reduce a side effect of acyclovir. Useful additional active ingredients include those suitable for topical use. In some embodiments, such additional active ingredient can be dissolved or partially suspended in the emulsified gel formulation. For example, in some embodiments, the emulsified gel formulation can include one or more additional active ingredients selected from anti-allergic medications, glucocorticoids, corticosteroids, anti-inflammatory agents, pain relievers, local anesthetics, and combinations thereof. In some embodiments, the emulsified gel formulation can include one or more additional active ingredients selected from selected from 2-deoxy-D-glucose, oxatamide, betamethasone, valerate, dexamethasone, triamcinolone acetonide, clobetasone butyrate, hydrocortisone, triamcinolone, flurbiprofen, ketorolace, lidocaine, benzocaine, articaine, chlorprocaine, cocaine, dydloninem, proparacaine, mepivacaine, prilocalne, procaine, tetracaine, pramoxin, and combinations thereof. In some embodiments, the emulsified gel formulation can include a corticosteroid, such as a glucocorticoid, for example, hydrocortisone.

In some embodiments, the emulsified gel formulation can also include an antioxidant or preservative. For example, in some embodiments, the emulsified gel formulation can include an antioxidant or preservative selected from butylated hydroxytoluene, phenoxyethanol, sodium metabisulfite, EDTA, ascorbic acid, and combinations thereof. In some embodiments, the emulsified gel formulation comprises phenoxyethanol. When present, the antioxidant or preservative is typically included in an amount of about 0.05% to about 5% (e.g., about 0.1%, about 0.5%, about 1%, about 2%, about 5%, or any ranges between the recited values) by weight of the emulsified gel formulation.

Other suitable excipients useful in the preparation of the emulsified gel formulations include humectants, sweeteners, flavorings, penetration enhancers, plasticizers, anti-irritants, emollients, surfactants, drug release modifiers, etc. These excipients are within the knowledge of those skilled in the art, and can be found, for example, in the Handbook of Pharmaceutical Excipients ($7^{th}$ Ed. 2012). In some embodiments, the emulsified gel formulations can also be free of or substantially free of an anionic surfactant, such as a fatty acid salt or a fatty sulfate salt.

Emulsified Gel Formulation Comprising Transcutol

The use of Transcutol (diethylene glycol monoethyl ether) in emulsified aqueous gel formulations herein was also found to be beneficial, for example, for achieving a desired acyclovir permeation profile. For example, as shown in the Examples section herein and FIG. 3, the emulsified gel EG04 (0.18%), which has almost 45% Transcutol, achieved a higher acyclovir permeation through the 1 $cm^2$ skin dosing area into citrate/phosphate buffer pH 4.0 at any time point post application up to 19 hours following application than Zovirax® Cream 5% as measured in the in vitro permeation studies.

In some embodiments, the present disclosure provides an emulsified gel formulation comprising: a) acyclovir in an amount of about 0.05% to about 0.5% by weight of the emulsified gel formulation; b) water; c) diethylene glycol monoethyl ether; d) an oil; e) an emulsifier; and f) a gel-forming agent. However, in some embodiments, the acyclovir can also be included at a higher concentration. For example, in some embodiments, the present disclosure provides an emulsified gel formulation comprising: a) acyclovir in an amount of about 0.05% to about 5% by weight of the emulsified gel formulation; b) water; c) diethylene glycol monoethyl ether; d) an oil; e) an emulsifier; and f) a gel-forming agent.

In some embodiments, the acyclovir can be present in an amount of about 0.1% to about 0.3%, such as about 0.1%, about 0.15%, about 0.2%, about 0.25%, or about 0.3%, or any range between the recited values, such as about 0.15-0.25%, by weight of the emulsified gel formulation. Typically, the acyclovir can be included in the emulsified gel formulation in an amount such that it can be dissolved in the emulsified gel formulation. In other words, in a typical embodiment, the emulsified gel formulation is free or substantially free of acyclovir in a solid form, such as with no visible (macroscopically or microscopically) suspended acyclovir particles or crystals. In some embodiments, the emulsified gel formulation can include acyclovir in an amount not more than the maximum solubility of acyclovir in the solvent system. In some embodiments, the emulsified gel formulation can include acyclovir in an amount substantially equal to the maximum solubility of acyclovir in the solvent system.

The emulsified gel formulation typically also includes a low molecular weight polyethylene glycol. However, in some embodiments, the emulsified gel formulation can also be free of such low molecular weight polyethylene glycol. When present, the low molecular weight polyethylene glycol is typically chosen from those that are liquids at room temperature. In some embodiments, the low molecular weight polyethylene glycol has an average molecular weight less than 1000, for example, less than 700, such as PEG 400.

Various amounts of low molecular weight polyethylene glycol can be suitably included in the emulsified gel formulation herein. For example, in some embodiments, the emulsified gel formulation can have a weight ratio of diethylene glycol monoethyl ether to the low molecular weight polyethylene glycol (e.g., PEG 400) ranging from about 20:1 to about 1:5, for example, about 20:1, about 15:1, about 10:1, about 5:1, about 1:1, about 1:2, or about 1:5, or any ranges in between the recited values. In some preferred embodiments, the emulsified gel formulation can have a weight ratio of diethylene glycol monoethyl ether to the low molecular weight polyethylene glycol (e.g., PEG 400) ranging from about 10:1 to about 2:1, such as about 6:1, about 5:1, about 4:1, about 3:1, about 2:1, or any ranges in between the recited values.

Water is typically included in the emulsified gel formulation at a weight ratio to diethylene glycol monoethyl ether ranging from about 10:1 to about 1:10, more typically, from about 5:1 to about 1:5, such as about 1:1, about 1:1.5, about 1:2, about 1:3, or any ranges between the recited values.

In some embodiments, the emulsified gel formulation comprises a solvent system that comprises, consists essentially of, or consists of water, diethylene glycol monoethyl ether, and the low molecular weight polyethylene glycol (e.g., PEG 400). In some embodiments, the emulsified gel formulation can also include one or more additional solvents, such as the water-miscible organic solvents described herein. For example, in some embodiments, the emulsified gel formulation can also include propylene glycol. However, in some embodiments, the emulsified gel formulation can also be free of propylene glycol. In some embodiments, the emulsified gel formulation can also include DMSO. In some embodiments, the emulsified gel formulation can be free of DMSO.

In some embodiments, the emulsified gel formulation comprises water, diethylene glycol monoethyl ether, and PEG 400. In some embodiments, the emulsified gel formulation comprises by weight of the emulsified gel formulation, water in an amount of about 25-65% (e.g., about 25%, about 30%, about 35%, about 40%, about 45%, about 50%, about 60%, about 65%, or any ranges in between the recited values such as about 25-60%, about 30-60%, about 30-50%, etc.), diethylene glycol monoethyl ether in an amount of about 25-70% (e.g., about 25%, about 30%, about 35%, about 40%, about 45%, about 50%, about 55%, about 60%, about 65%, about 70%, or any ranges in between the recited values such as about 25-60%, about 35-70%, about 30-50%, etc.), and PEG 400 in an amount of about 0-20% (e.g., about 1%, about 5%, about 10%, about 15%, about 20%, or any ranges in between the recited values such as about 5-20%, about 5-15%, about 10-20%, etc.). In some embodiments, the weight ratio of diethylene glycol monoethyl ether to PEG 400 ranges from about 20:1 to about 1:5, for example, about 20:1, about 15:1, about 10:1, about 5:1, about 1:1, about 1:2, or about 1:5, or any ranges in between the recited values. In some preferred embodiments, the weight ratio of diethylene glycol monoethyl ether to the PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 2:1 to about 1:2, such as about 2:1, about 1.5:1, about 1:1, about 1:1.5, about 1:2, or any ranges between the recited values.

In some specific embodiments, the emulsified gel formulation comprises: a) acyclovir in an amount of about 0.1% to about 0.3% (e.g., about 0.15%, about 0.2%, about 0.25%, or about 0.15-0.25%) by weight of the emulsified gel formulation; b) water in an amount of about 30-50% (e.g., about 30%, about 35%, about 40%, about 45%, about 50%, or any ranges in between the recited values) by weight of the emulsified gel formulation; c) diethylene glycol monoethyl ether in an amount of about 30-60% (e.g., about 30%, about 35%, about 40%, about 45%, about 50%, about 55%, about 60%, or any ranges in between the recited values such as about 45-55%, about 40-60%, about 35-55%, etc.) by weight of the emulsified gel formulation; d) PEG 400 in an amount of about 5-15% (e.g., about 5%, about 10%, about 15%, or any ranges in between the recited values) by weight of the emulsified gel formulation; e) an oil; f) an emulsifier; and g) a gel forming agent. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.5:1 to about 1:2, such as about 1.2:1, about 1:1, about 1:1.5, about 1:2, or any ranges between the recited values. Suitable pH and other optionally ingredients include any of those described herein in any combination.

Typically, the oil in the emulsified gel formulation is a fatty ester (e.g., mixed esters of palm oil or coconut oil, such as Crodamol™ GTCC). In some embodiments, the oil can be included in an amount of about 1% to about 20% (e.g., about 5%, about 10%, about 15%, about 20%, or any ranges between the recited values such as about 5-15% or about 5-20%) by weight of the emulsified gel formulation. For example, in some specific embodiments, the emulsified gel formulation comprises: a) acyclovir in an amount of about 0.1% to about 0.3% (e.g., about 0.15%, about 0.2%, about 0.25%, or about 0.15-0.25%) by weight of the emulsified gel formulation; b) water in an amount of about 30-50% (e.g., described herein) by weight of the emulsified gel formulation; c) diethylene glycol monoethyl ether in an amount of about 30-60% (e.g., described herein) by weight of the emulsified gel formulation; d) PEG 400 in an amount of about 5-15% (e.g., described herein) by weight of the emulsified gel formulation; e) a triglyceride of caprylic and/or capric acid or a mixed ester of palm oil or coconut oil such as Crodamol™ GTCC, in an amount of about 5% to about 15% (e.g., about 5%, about 10%, about 15%, or any ranges between the recited values) by weight of the emulsified gel formulation; f) an emulsifier; and g) a gel-forming agent. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.5:1 to about 1:2, such as about 1.2:1, about 1:1, about 1:1.5, about 1:2, or any ranges between the recited values. Suitable pH and other optionally ingredients include any of those described herein in any combination.

Suitable gel-forming agents and emulsifiers for the emulsified gel formulations include any of those described herein. Typically, the gel-forming agent is included in the emulsified gel formulation in a gel-forming effective amount. In some embodiments, the gel forming agent is in an amount of about 0.1% to about 5% (e.g., about 0.1%, about 0.5%, about 1%, about 2%, about 5%, or any ranges between the recited values such as about 0.1-2% or about 0.1-1%) by weight of the emulsified gel formulation. In some embodiments, the gel forming agent can be a crosslinked polyacrylic acid, such as a crosslinked polyacrylic acid with allyl sucrose or allyl pentaerythritol, such as Carbopol® 980.

In some embodiments, the emulsifier and the gel-forming agent can be the same agent. For example, in some embodiments, the emulsifier can comprise an acrylamide and acryloyldimethyl taurate copolymer and a non-ionic surfactant. In some embodiments, the emulsifier comprises an acrylamide and sodium acryloyldimethyl taurate copolymer dispersed in isohexadecane and a non-ionic surfactant (e.g., polysorbate, such as polysorbate 80), such as Sepineo™ P600. In some embodiments, the emulsifier and gel-forming agent can also be different. In some embodiments, the emulsifier is in an amount of about 1% to about 10% (e.g., about 1%, about 5%, about 10%, or any ranges between the recited values) by weight of the emulsified gel formulation. For example, in some specific embodiments, the emulsified gel formulation comprises: a) acyclovir in an amount of about 0.1% to about 0.3% (e.g., about 0.15%, about 0.2%, about 0.25%, or about 0.15-0.25%) by weight of the emulsified gel formulation; b) water in an amount of about 30-50% (e.g., described herein) by weight of the emulsified gel formulation; c) diethylene glycol monoethyl ether in an amount of about 30-60% (e.g., described herein) by weight of the emulsified gel formulation; d) PEG 400 in an amount of about 5-15% (e.g., described herein) by weight of the emulsified gel formulation; e) a triglyceride of caprylic and/or capric acid or a mixed ester of palm oil or coconut oil such as Crodamol™ GTCC, in an amount of about 5% to about 15% (e.g., about 5%, about 10%, about 15%, or any ranges between the recited values) by weight of the emulsified gel formulation; and f) an emulsifier comprising an acrylamide and sodium acryloyldimethyl taurate copolymer, e.g., dispersed in isohexadecane, and a non-ionic surfactant (e.g., polysorbate, such as polysorbate 80), such as Sepineo™ P600, in an amount of about 1% to about 10% (e.g., about 1%, about 5%, about 10%, or any ranges between the recited values) by weight of the emulsified gel formulation. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.5:1 to about 1:2, such as about 1.2:1, about 1:1, about 1:1.5, about 1:2, or any ranges between the recited values. Suitable pH and other optionally ingredients include any of those described herein in any combination.

The pH of the emulsified gel formulation is typically from about 4 to about 8. In some embodiments, the pH of the emulsified gel formulation can be from about 5 to about 7, for example, about 6 to about 6.5.

In some embodiments, acyclovir can be included in the emulsified gel formulation as the only active ingredient. However, in some embodiments, acyclovir can also be included together with an additional active ingredient in the emulsified gel formulation, e.g., as described herein. Such additional active ingredient can be, for example, another antiviral agent, or an agent that can supplement the action of acyclovir and/or reduce a side effect of acyclovir. Useful additional active ingredients include those suitable for topical use. In some embodiments, such additional active ingredient can be dissolved or partially suspended in the emulsified gel formulation.

In some embodiments, the emulsified gel formulation can also include an antioxidant or preservative. For example, in some embodiments, the emulsified gel formulation can include an antioxidant or preservative selected from butylated hydroxytoluene, phenoxyethanol, sodium metabisulfite, EDTA, ascorbic acid, and combinations thereof. In some embodiments, the emulsified gel formulation comprises phenoxyethanol. When present, the antioxidant or preservative is typically included in an amount of about 0.05% to about 5% (e.g., about 0.1%, about 0.5%, about 1%, about 2%, about 5%, or any ranges between the recited values) by weight of the emulsified gel formulation.

Other suitable excipients useful in the preparation of the aqueous gel formulations include humectants, sweeteners, flavorings, penetration enhancers, plasticizers, anti-irritants, emollients, surfactants, drug release modifiers, etc. These excipients are within the knowledge of those skilled in the art, and can be found, for example, in the Handbook of Pharmaceutical Excipients ($7^{th}$ Ed. 2012). In some embodiments, the emulsified gel formulations can also be free of or substantially free of an anionic surfactant, such as a fatty acid salt or a fatty sulfate salt.

In some specific embodiments, the emulsified gel formulation comprises: a) acyclovir in an amount of about 0.1% to about 0.3% (e.g., about 0.15%, about 0.2%, about 0.25%, or about 0.15-0.25%) by weight of the emulsified gel formulation; b) water in an amount of about 30-50% (e.g., described herein) by weight of the emulsified gel formulation; c) diethylene glycol monoethyl ether in an amount of about 30-60% (e.g., described herein) by weight of the emulsified gel formulation; d) PEG 400 in an amount of about 5-15% (e.g., described herein) by weight of the emulsified gel formulation; e) a triglyceride of caprylic and/or capric acid or a mixed ester of palm oil or coconut oil, such as Crodamol™ GTCC, in an amount of about 5% to about 15% (e.g., about 5%, about 10%, about 15%, or any ranges between the recited values) by weight of the emulsified gel formulation; f) an emulsifier comprising an acrylamide and sodium acryloyldimethyl taurate copolymer, e.g., dispersed in isohexadecane, and a non-ionic surfactant (e.g., polysorbate, such as polysorbate 80), such as Sepineo™ P600, in an amount of about 1% to about 10% (e.g., about 1%, about 5%, about 10%, or any ranges between the recited values) by weight of the emulsified gel formulation; and g) phenoxyethanol in an amount of about 0.05% to about 2% (e.g., about 0.1%, about 0.5%, about 1%, about 2%, or any ranges between the recited values) by weight of the emulsified gel formulation. In some embodiments, the weight ratio of diethylene glycol monoethyl ether to PEG 400 ranges from about 10:1 to about 2:1, such as about 6:1, about 5:1, about 4:1, about 3:1, about 2:1, or any ranges in between the recited values. In some preferred embodiments, the weight ratio of water to diethylene glycol monoethyl ether ranges from about 1.5:1 to about 1:2, such as about 1.2:1, about 1:1, about 1:1.5, about 1:2, or any ranges between the recited values. Suitable pH and other optionally ingredients include any of those described herein in any combination.

In some specific embodiments, the emulsified gel formulation comprises the following ingredients (by weight of the emulsified gel formulation): acyclovir (about 0.18%), water (about 34%), PEG 400 (about 7.8%), phenoxyethanol (about 1%), Transcutol, i.e., diethylene glycol monoethyl ether (about 42.8%), Sepineo™ P600 (about 4%), Crodamol™ GTCC (about 10%), optional H adjusting agent, with the total amount being 100%. The pH is typically adjusted to about 5-7, such as about 5.5-6.5 or 6-6.5.

Method of Preparing Emulsified Gel Formulation

In some embodiments, the present disclosure also provides a method of preparing an emulsified gel formulation described herein. The emulsified gel formulation described herein (e.g., those including Transcutol) can be readily prepared by those skilled in the art in view of the present disclosure. In one typical embodiment, the method comprises 1) mixing and optionally dissolving acyclovir with aqueous phase ingredients of the emulsified gel formulation to form an aqueous acyclovir solution or suspension; 2) mixing the oil phase ingredients (e.g., oil, emulsifier) and optionally the gel-forming agent with the aqueous acyclovir solution or suspension to form an emulsified aqueous gel; and 3) optionally adjusting the pH of the emulsified aqueous gel.

For example, in some embodiments, the method is for preparing the emulsified gel formulation comprising: a) acyclovir in an amount of about 0.1% to about 0.3% (e.g., about 0.15%, about 0.2%, about 0.25%, or about 0.15-0.25%) by weight of the emulsified gel formulation; b) water in an amount of about 30-50% (e.g., described herein) by weight of the emulsified gel formulation; c) diethylene glycol monoethyl ether in an amount of about 30-60% (e.g., described herein) by weight of the emulsified gel formulation; d) PEG 400 in an amount of about 5-15% (e.g., described herein) by weight of the emulsified gel formulation; e) a triglyceride of caprylic and/or capric acid or a mixed ester of palm oil or coconut oil, such as Crodamol™ GTCC, in an amount of about 5% to about 15% (e.g., about 5%, about 10%, about 15%, or any ranges between the recited values) by weight of the emulsified gel formulation; f) an emulsifier comprising an acrylamide and sodium acryloyldimethyl taurate copolymer, e.g., dispersed in isohexadecane, and a non-ionic surfactant (e.g., polysorbate, such as polysorbate 80), such as Sepineo™ P600, in an amount of about 1% to about 10% (e.g., about 1%, about 5%, about 10%, or any ranges between the recited values) by weight of the emulsified gel formulation; and g) phenoxyethanol in an amount of about 0.05% to about 2% (e.g., about 0.1%, about 0.5%, about 1%, about 2%, or any ranges between the recited values) by weight of the emulsified gel formulation, the method comprises: 1) dissolving the acyclovir in a mixture comprising water, diethylene glycol monoethyl ether, PEG 400, and the optional antioxidant/preservative to form an aqueous acyclovir solution; 2) adding the triglyceride or mixed ester and the emulsifier to the aqueous acyclovir solution to form an emulsified aqueous gel; and 3) optionally adjusting the pH of the emulsified aqueous gel. In some embodiments, the pH is adjusted to about 4 to about 8, e.g., about 5-7 or about 5.5-6.5 or 6-6.5, for example, with an alkali hydroxide base such as NaOH. Typically, after the pH is adjusted to a desired range, a second addition of water can be conducted, and the mixture can be mixed to form a homogenous mixture. The appropriate amount of each ingredient varies according to the final emulsified gel formulation to be prepared. Typically, all aqueous phase ingredients are mixed with the acyclovir to form the aqueous acyclovir solution in step 1) or added to the acyclovir solution of step 1), except a portion of the water, optional pH adjusting agent, and optionally the gel forming agent. A representative procedure is described in the Examples section.

It should be noted that the aqueous emulsified gel formulation and aqueous acyclovir solution prepared by the methods herein are also novel compositions of the present disclosure.

Non-Aqueous Gel Formulation

In some embodiments, the present disclosure also provides a non-aqueous gel formulation. The non-aqueous gel formulations typically are formulated for topical use, which can include acyclovir dissolved or partially suspended in a non-aqueous gel. Like the aqueous gel formulations described herein, acyclovir typically can be included in the non-aqueous gel formulations in an amount of less than 1% by weight. However, in some embodiments, the acyclovir can also be included at a higher concentration. For example, in some embodiments, the acyclovir can be included in the nonaqueous gel formulations in an amount of about 0.05% to about 5% (e.g., about 1-5%, about 2-5%, about 2-4%, etc.) by weight. In some embodiments, the acyclovir can be included in an amount of about 0.5% or less, about 0.4% or less, about 0.3% or less, about 0.2% or less, or about 0.1% or less by weight. In some embodiments, the acyclovir can be included in the non-aqueous gel formulation in an amount of about 0.02%, about 0.05%, about 0.1%, about 0.2%, about 0.3%, about 0.4%, or about 0.5% by weight, or any ranges between the recited values. For example, in one embodiment, the acyclovir can be present in an amount of about 0.05% to about 0.5% by weight.

The non-aqueous gel typically includes a non-aqueous organic solvent system and an effective amount of a gel-forming agent. The solvent system is generally selected to achieve a good solubility of acyclovir and/or an enhanced skin permeation of acyclovir, causing little to no skin irritation when applied.

Typically, the non-aqueous solvent system forms most of the weight of the aqueous gel formulation. In some embodiments, the solvent system forms about 70%, about 80%, about 90%, about 95%, or about 99%, or any ranges between the recited values, by weight of the non-aqueous gel formulation.

Various organic solvents can be used for the non-aqueous gel formulations of the present disclosure. Non-limiting useful organic solvents include propylene glycol, glycerol, Transcutol®, dimethyl sulfoxide (DMSO), and a low molecular weight polyethylene glycol. For example, in some embodiments, the solvent system includes propylene glycol, e.g., in an amount of about 5% to about 30% (e.g., about 5%, about 10%, about 20%, about 30%, or any ranges between the recited values) by weight of the non-aqueous gel formulation. In some embodiments, the solvent system includes Transcutol®, e.g., in an amount of about 10% to about 60% (e.g., about 20%, about 30%, about 40%, about 50%, or any ranges between the recited values) by weight of the non-aqueous gel formulation. In some embodiments, the solvent system includes a low molecular weight polyethylene glycol (PEG), such as PEG 200-1000, such as PEG 200, PEG 400, PEG 450, PEG 500, PEG 600, etc., e.g., in an amount of about 5% to about 40% (e.g., about 10%, about 20%, about 30%, about 40%, or any ranges between the recited values) by weight of the non-aqueous gel formulation. In some embodiments, the solvent system includes more than one, such as two, three, or four organic solvents. In some embodiments, the solvent system includes at least two solvents selected from propylene glycol, Transcutol® and a low molecular weight PEG (e.g., PEG 400). In some embodiments, the solvent system includes a combination of propylene glycol, Transcutol®, DMSO, and a low molecular weight PEG (e.g., PEG 400). When two or more solvents are included, the ratio of these solvents can vary. For example, in a solvent system having a combination of propylene glycol, Transcutol®, DMSO, and PEG 400, any one of the solvents can be in an amount of about 5-85% (e.g., 10-70%) of the total amount of the solvents. In some embodiments, the solvent system can also be free or substantially free of a certain solvent. For example, in some embodiments, the solvent system can be free or substantially free of ethanol. In some embodiments, the solvent system can be free or substantially free of isopropanol. In some embodiments, the solvent system can be free or substantially free of DMSO. In some embodiments, the solvent system can be free or substantially free of glycerol. In some embodiments, the solvent system can be free or substantially free of propylene glycol.

The gel-forming agent for the non-aqueous gel formulation can be any of those known in the art suitable for topical use. Non-limiting suitable gel-forming agents include those described herein. Typically, the gel-forming agent is included in the non-aqueous gel formulation in a gel-forming effective amount. In some embodiments, the gel forming agent is in an amount of about 0.1% to about 5% (e.g., about 0.1%, about 0.5%, about 1%, about 2%, about 5%, or any ranges between the recited values) by weight of the aqueous gel formulation. In some embodiments, the gel forming agent can be a cellulose derivative such as hydroxypropyl cellulose.

In some specific embodiments, the non-aqueous gel formulation comprises: a) acyclovir in an amount of about 0.1% to about 0.3% by weight (e.g., about 0.15% to about 0.25%) of the non-aqueous gel formulation; b) diethylene glycol monoethyl ether in an amount of about 10-40% (e.g., about 10%, about 20%, about 30%, about 40%, or any range between the recited values such as about 20-30%) by weight of the non-aqueous gel formulation; c) PEG 400 in an amount of about 30-70% (e.g., about 30%, about 40%, about 50%, about 60%, about 70%, or any range between the recited values such as about 40-60%) by weight of the non-aqueous gel formulation; d) propylene glycol in an amount of about 5% to about 25% (e.g., about 5%, about 10%, about 15%, about 20%, about 25%, or any ranges between the recited values such as about 5-15%) by weight of the non-aqueous gel formulation; e) DMSO in an amount of about 5% to about 25% (e.g., about 5%, about 10%, about 15%, about 20%, about 25%, or any ranges between the recited values such as about 5-15%) by weight of the non-aqueous gel formulation; f) a gel-forming agent, such as hydroxypropyl cellulose, in an amount of about 0.1% to about 5% (e.g., about 0.1%, about 0.5%, about 1%, about 2%, about 5%, or any ranges between the recited values such as about 0.5-1.5%) by weight of the non-aqueous gel formulation; and g) an antioxidant or preservative, such as phenoxyethanol, in an amount of about 0.05% to about 2% (e.g., about 0.1%, about 0.5%, about 1%, about 2%, or any ranges between the recited values) by weight of the non-aqueous gel formulation. In some embodiments, the weight ratio of diethylene glycol monoethyl ether to PEG 400 ranges from about 2:1 to about 1:10, such as about 1:1, about 1:2, about 1:3, or any ranges in between the recited values. In some preferred embodiments, the weight ratio of propylene glycol to diethylene glycol monoethyl ether ranges from about 1:1 to about 1:5, such as about 1:1, about 1:2, about 1:3, about 1:5, or any ranges between the recited values. Suitable other optionally ingredients include any of those described herein in any combination.

In some specific embodiments, the non-aqueous gel formulation comprises the following ingredients (by weight of the non-aqueous gel formulation): acyclovir (about 0.16%), PEG 400 (about 54%), phenoxyethanol (about 1%), Transcutol, i.e., diethylene glycol monoethyl ether (about 25%), DMSO (about 10%), propylene glycol (about 10%), hydroxypropyl cellulose (about 1%), with the total amount being 100%.

In some embodiments, acyclovir can be included in the nonaqueous gel formulation as the only active ingredient. However, in some embodiments, acyclovir can also be included together with an additional active ingredient in the nonaqueous gel formulation. Such additional active ingredient can be, for example, another antiviral agent, or an agent that can supplement the action of acyclovir and/or reduce a side effect of acyclovir. Useful additional active ingredients include those suitable for topical use. In some embodiments, such additional active ingredient can be dissolved or partially suspended in the nonaqueous gel formulation. For example, in some embodiments, the nonaqueous gel formulation can include one or more additional active ingredients selected from anti-allergic medications, glucocorticoids, corticosteroids, anti-inflammatory agents, pain relievers, local anesthetics, and combinations thereof. In some embodiments, the nonaqueous gel formulation can include one or more additional active ingredients selected from selected from 2-deoxy-D-glucose, oxatamide, betamethasone, valerate, dexamethasone, triamcinolone acetonide, clobetasone butyrate, hydrocortisone, triamcinolone, flurbiprofen, ketorolace, lidocaine, benzocaine, articaine, chlorprocaine, cocaine, dydloninem, proparacaine, mepivacaine, prilocalne, procaine, tetracaine, pramoxin, and combinations thereof. In some embodiments, the nonaqueous gel formulation can include a corticosteroid, such as a glucocorticoid, for example, hydrocortisone.

Method of Preparing Non-Aqueous Gel Formulation

In some embodiments, the present disclosure also provides a method of preparing a non-aqueous formulation described herein. The non-aqueous gel formulation described herein can be readily prepared by those skilled in the art in view of the present disclosure. In one typical embodiment, the method comprises 1) mixing and optionally dissolving acyclovir with other ingredients of the non-aqueous gel formulation to form a non-aqueous acyclovir solution or suspension; 2) mixing the gel-forming agent with the non-aqueous acyclovir solution or suspension to form the non-aqueous gel formulation. The appropriate amount of each ingredient varies according to the final non-aqueous gel formulation to be prepared. Typically, all ingredients are mixed with the acyclovir to form the non-aqueous acyclovir solution in step 1) or added to the non-aqueous acyclovir solution of step 1), except the gel forming agent, which is typically added to the non-aqueous acyclovir solution to form a non-aqueous gel. A representative procedure is described in the Examples section.

It should be noted that the non-aqueous gel formulation and non-aqueous acyclovir solution prepared by the methods herein are also novel compositions of the present disclosure.

The gel formulations of the present disclosure can also be characterized by certain skin permeation profiles. For example, in any of the embodiments described herein, when tested according to the method described in Example 3B, the gel formulation provides an in vitro permeation rate per unit area of about 20% to about 500% (e.g., about 50%, about 100%, about 200%, about 500%, or any ranges between the recited values) of that of a dose equivalent cream or gel formulation containing 5% acyclovir by weight, e.g., the marketed product Zovirax® Cream 5%. In some embodiments, when applied to a subject/user, the gel formulation can also topically deliver acyclovir to the subject/user at a permeation rate per unit area of about 20% to about 500% (e.g., about 50%, about 100%, about 200%, about 500%, or any ranges between the recited values) of that of a dose equivalent cream or gel formulation containing 5% acyclovir by weight, e.g., the marketed product Zovirax® Cream 5%. In some embodiments, the gel formulation herein can deliver a much higher level of acyclovir to a subject/user compared to that of Zovirax® Cream 5%, as shown by the dermal open flow microperfusion studies herein, see e.g., FIGS. 5 and 6. In some embodiments, when applied to a subject/user, the gel formulation can also topically deliver acyclovir to the subject/user at a permeation rate per unit area of about 20% to about 500-fold (e.g., about 100%, about 10-fold, about 100-fold, about 200-fold, about 500-fold or any ranges between the recited values) greater than that of a dose equivalent cream or gel formulation containing 5% acyclovir by weight, e.g., the marketed product Zovirax® Cream 5%.

The gel formulations of the present disclosure can also be characterized by certain shelf stabilities. For example, in any of the embodiments described herein, the gel formulation can also be shelf stable, which can mean that, upon storage of the gel formulation for 2 weeks or more at 25° C. or 40° C., (1) the amount of acyclovir in the gel formulation remains substantially unchanged (e.g., with less than 10% degradation, less than 5% degradation, or less than 1% degradation); and/or (2) no visible (macroscopically or microscopically) suspended acyclovir particles or crystals.

The gel formulations of the present disclosure can typically be prepared by mixing the ingredients (e.g., described herein) to form a solution or an emulsion, and then adding a gel-forming polymer to form an aqueous gel, an emulsified gel, or a non-aqueous gel. The acyclovir used for the gel formulations of the present disclosure can be non-micronized. In some cases, a small amount of acyclovir can be suspended in the solution or emulsion. In cases of an emulsified gel, an emulsifier is also typically added to stabilize the emulsion. The ingredients of the gel formulations, such as the solvent system, acyclovir load, antioxidants/preservatives, etc. are described herein and can be adjusted to achieve a desired permeation profile. It should be noted that the solution or emulsion prior to adding the gel-forming polymer are also novel composition of the present disclosure. In some embodiments, the emulsion can also be formulated into a cream formulation, see e.g., CR05 in Table 3 of the present disclosure. In some embodiments, the solution, emulsion, or cream formulations can also be used for treating a disease or disorder where the gel formulations are indicated as useful.

Exemplified Topical Formulations

In some embodiments, the present disclosure also provides certain exemplified topical formulations, which include any of the specified formulations listed in Tables 3-5, 7, 9B, and 11 of the present disclosure. The placebo formulations prepared herein are also novel compositions of the present disclosure. For example, the placebo formulations can be used to prepare gel formulations with higher concentration of acyclovir formulations, gel formulations with other active ingredients, such as other antiviral compounds including penciclovir, valacyclovir, etc.

For example, in some embodiments, the present disclosure provides exemplified aqueous gel formulation that is non-emulsified:

| Ingredient | Percentage by weight | | |
|---|---|---|---|
| | Typical | More specific | Further Specific |
| Acyclovir | <1% | 0.05-0.5% | 0.15-0.25% |
| Water | 20-80% | 25-65% | 30-50% (e.g., 39%) |
| Water-miscible organic solvents (e.g., Transcutol ®, propylene glycol, and PEG 400) | 15-70% | 30-70% | 45-70% (e.g., 60%) |
| Gel-forming agent (e.g., Carbopol ® 980) | 0.1-5% | 0.1-2% | 0.1-1% (e.g., 0.5%) |
| Others (Antioxidant/ preservative, such as phenoxyethanol) | 0-5% | 0.1-2% | 0.5-1.5% (e.g., 1%) |
| pH | 4-8 | 5-7 | 6.0-6.5 |

The numeric values in the table should be understood as preceded by the term "about." Other ingredients can be optionally included. In some embodiments, the water-miscible organic solvents include Transcutol® and propylene glycol. In some embodiments, the water-miscible organic solvents include Transcutol® and PEG 400. In some embodiments, the water-miscible organic solvents include Transcutol®, propylene glycol, and PEG 400. In some embodiments, the water-miscible organic solvents are free of propylene glycol. In some embodiments, the water-miscible organic solvents are free of DMSO. In some embodiments, the aqueous gel formulation can be characterized by any of the permeation profile described herein. In some embodiments, the aqueous gel formulation is shelf stable.

For example, in some embodiments, the present disclosure provides exemplified aqueous emulsified gel formulation:

| Ingredient | Percentage by weight | | |
|---|---|---|---|
| | Typical | More specific | Further Specific |
| Acyclovir | <1% | 0.05-0.5% | 0.15-0.25% |
| Water | 20-80% | 25-65% | 30-50% (e.g., 34%) |
| Water-miscible organic solvents (e.g., Transcutol ®, propylene glycol, and PEG 400) | 15-70% | 30-70% | 35-60% (e.g., 50%) |
| oil (e.g., an emollient, such as fatty esters, Cromadol ™ GTCC) | 1-20% | 1-15% | 5-10% (e.g., 10%) |
| Gel-forming agent (e.g., Sepineo ™ P600) | 0.1-10% | 0.1-8% | 2-6% (e.g., 4%) |
| Emulsifier (e.g., Sepineo ™ P600) | 0.1-5% | 0.1-8% | 2-6% (e.g., 4%) |
| Others (Antioxidant/ preservative, such as phenoxyethanol) | 0-5% | 0.1-2% | 0.5-1.5% (e.g., 1%) |
| pH | 4-8 | 5-7 | 6.0-6.5 |

The numeric values in the table should be understood as preceded by the term "about." Other ingredients can be optionally included. In some embodiments, the water-miscible organic solvents include Transcutol® and propylene glycol. In some embodiments, the water-miscible organic solvents include Transcutol® and PEG 400. In some embodiments, the water-miscible organic solvents include Transcutol®, propylene glycol, and PEG 400. In some embodiments, the water-miscible organic solvents are free of propylene glycol. In some embodiments, the water-miscible organic solvents are free of DMSO. In some embodiments, the aqueous gel formulation can be characterized by any of the permeation profile described herein. In some embodiments, the aqueous gel formulation is shelf stable.

For example, in some embodiments, the present disclosure provides exemplified non-aqueous gel formulation:

| Ingredient | Percentage by weight | | |
|---|---|---|---|
| | Typical | More specific | Further Specific |
| Acyclovir | <1% | 0.05-0.5% | 0.15-0.25% |
| Solvents (e.g., Transcutol ®, propylene glycol, DMSO, and PEG 400) | 60-99% | 70-99% | 85-98% (e.g., 98%) |
| Gel-forming agent (e.g., HPC) | 0.1-5% | 0.1-2% | 0.5-1.5% (e.g., 1%) |
| Others (Antioxidant/ preservative, such as phenoxyethanol) | 0-5% | 0-2% | 0-1.5% (e.g., 1%) |

The numeric values in the table should be understood as preceded by the term "about." Other ingredients can be optionally included. In some embodiments, the solvents include Transcutol® and propylene glycol. In some embodiments, the solvents include Transcutol® and PEG 400. In some embodiments, the solvents include Transcutol®, propylene glycol, DMSO, and PEG 400. In some embodiments, the solvents are free of propylene glycol. In some embodiments, the solvents are free of DMSO. In some embodiments, the non-aqueous gel formulation can be characterized by any of the permeation profile described herein. In some embodiments, the non-aqueous gel formulation is shelf stable.

Methods of Treatment

Some embodiments of the present disclosure are also directed to methods of topically applying the gel formulations of the present disclosure. As discussed herein, the gel formulations of the present disclosure have several advantages over the marketed product Zovirax® Cream 5%. For example, in various embodiments, representative gel formulations of the present disclosure can overcome some of the short comings of the Zovirax® Cream 5% (e.g., poor solubility of the drug in the commercial product (<0.5%), large particle range of acyclovir, and poor permeability) and can enhance patient compliance.

The gel formulation of the present disclosure can be used for treating or preventing any diseases or disorders for which the active ingredient is indicated for. For example, the gel formulation of the present disclosure can be used for treating any disease or disorder that acyclovir has been shown to be useful. Such diseases or disorders are typically associated with HSV and/or VZV, which include but are not limited to genital herpes simplex, neonatal herpes simplex, cold sores, shingles, acute chickenpox in immunocompromised patients, acute mucocutaneous HSV infections in immunocompromised patients, herpes of the eye and herpes simplex blepharitis, etc.

In some embodiments, the present disclosure provides a method of treating or preventing herpes labialis (cold sores) in a subject in need thereof, the method comprising topically applying to the subject an effective amount of the aqueous gel or emulsified gel formulation of the present disclosure or the non-aqueous gel formulation of the present disclosure. In some embodiments, the herpes labialis (cold sores) is a recurrent herpes labialis. In some embodiments, the aqueous gel, emulsified gel, or non-aqueous gel formulation of the present disclosure can be administered topically to the affected area in a single daily dose or in multiple doses per day, e.g., 2-4 times a day. In some embodiments, treatment regimen can require administration from a single dose up to multiple daily doses for an extended period of time, for example, for several days or from one to two weeks. Other treatment regimens are also suitable and can be adjusted by those skilled in the art. The amount of acyclovir administered per dose or the total amount administered will depend on such factors as the nature and severity of the infection, the age and general health of the subject. In some embodiments, the subject is an immunocompetent adult or adolescents 12 years of age and older.

In some embodiments, the present disclosure provides a method of treating herpes viral infections of the skin or mucosa of a subject in need thereof, the method comprising topically applying to the subject an effective amount of the aqueous gel or emulsified gel formulation of the present disclosure or the non-aqueous gel formulation of the present disclosure. The aqueous or non-aqueous gel formulation of the present disclosure can be administered topically to the affected area in a single daily dose or in multiple doses per day, e.g., 2-4 times a day. Treatment regimen can require administration from a single dose up to multiple daily doses for an extended period of time, for example, for several days or from one to two weeks. Other treatment regimens are also suitable and can be adjusted by those skilled in the art. The amount of acyclovir administered per dose or the total amount administered will depend on such factors as the nature and severity of the infection, the age and general health of the subject. In some embodiments, the subject is an immunocompetent adult or adolescents 12 years of age and older. In some embodiments, the herpes viral infection is herpes simplex virus (HSV) infection. In some embodiments, the herpes viral infection is HSV-1 and/or HSV-2 infection. In some embodiments, the herpes infection is varicella-zoster virus (VZV) infection. In some embodiments, the herpes viral infection is a herpes zoster infection. In some embodiments, the herpes viral infection is herpes varicella infection.

In some embodiments, the present disclosure provides a method of treating an HSV infection outbreak, the method comprising topically applying the aqueous gel, emulsified gel, or non-aqueous gel formulation of the present disclosure to a subject in need thereof. In some embodiments, the subject is an immunocompetent adult or adolescents 12 years of age and older. In some embodiments, application of the aqueous gel, emulsified gel, or non-aqueous gel formulation of the present disclosure provides similar or better relief to a subject/user compared to a dose equivalent application of the marketed product Zovirax® Cream 5%.

In some embodiments, the present disclosure provides a method of reducing the duration of a herpes viral infection outbreak, the method comprising topically applying the aqueous gel, emulsified gel, or non-aqueous gel formulation of the present disclosure to a subject in need thereof. In some embodiments, the subject is an immunocompetent adult or adolescents 12 years of age and older. In some embodiments, the subject has latent infection of herpes simplex type 1 infection. In some embodiments, the subject has latent infection of herpes simplex type 2 infection. In some embodiments, the subject has an orofacial herpes viral infection.

In some embodiments, the present disclosure provides a method of administering acyclovir to a subject in need thereof, the method comprising topically applying the aqueous gel, emulsified gel, or non-aqueous gel formulation of the present disclosure to the subject.

The gel formulation of the present disclosure can be used as a monotherapy or used in a combination therapy. For example, in some embodiments, gel formulation of the present disclosure can be co-administered with an additional pharmaceutically active agent, either concurrently or sequentially in any order, to a subject in need thereof (e.g., a subject having a herpes viral infection as described herein). For example, in some embodiments, the additional pharmaceutically active agent(s) can be selected from anti-allergic medications, glucocorticoids, corticosteroids, anti-inflammatory agents, pain relievers, local anesthetics, and combinations thereof. In some embodiments, the additional pharmaceutically active agent(s) can be selected from 2-deoxy-D-glucose, oxatamide, betamethasone, valerate, dexamethasone, triamcinolone acetonide, clobetasone butyrate, hydrocortisone, triamcinolone, flurbiprofen, ketorolace, lidocaine, benzocaine, articaine, chlorprocaine, cocaine, dydloninem, proparacaine, mepivacaine, prilocalne, procaine, tetracaine, pramoxin, and combinations thereof. In some embodiments, the additional pharmaceutically active agent(s) can include a corticosteroid, such as a glucocorticoid, for example, hydrocortisone. The additional pharmaceutically active agent(s) can be included in the gel formulation of the present disclosure or be provided in a separate formulation.

Definitions

As used herein, the term "about" modifying an amount related to the invention refers to variation in the numerical quantity that can occur, for example, through routine testing and handling; through inadvertent error in such testing and handling; through differences in the manufacture, source, or purity of ingredients employed in the invention; and the like. As used herein, "about" a specific value also includes the specific value, for example, about 10% includes 10%. Whether or not modified by the term "about", the claims include equivalents of the recited quantities. In one embodiment, the term "about" means within 20% of the reported numerical value.

As used herein, the term "gel formulation(s) of the present disclosure" includes any of the aqueous gel formulations, emulsified gel formulations, and non-aqueous gel formulations described herein, including any of the specific gel formulations listed in Tables 3-5, 7, 9B, and 11 of the present disclosure. The gel formulation(s) of the present disclosure is typically formulated for topical use. In any of the embodiments described herein, unless specified or obvious from context, the gel formulation(s) of the present disclosure can be AG21 with the ingredients shown in Table 7. In any of the embodiments described herein, unless specified or obvious from context, the gel formulation(s) of the present disclosure can also be AG23 with the ingredients shown in Table 7. In any of the embodiments described herein, unless specified or obvious from context, the gel formulation(s) of the present disclosure can be EG04 with the ingredients shown in Table 7. In any of the embodiments described herein, unless specified or obvious from context, the gel formulation(s) of the present disclosure can be NA14 with the ingredients shown in Table 5. It should be understood that certain formulations are designated with a name including "-placebo" or "-HC", which are different from the formulations without such expressions. For example, AG21, which has about 0.2% acyclovir, is a different formulation from AG21-placebo which does not include any acyclovir. Similarly, AG23, which has about 0.2% acyclovir, is a different formulation from AG23-HC, which has about 5% acyclovir.

As used herein, the term "average molecular weight" of a polymer should be understood as referring to the number average molecular weight or weight average molecular weight, unless it is contrary to the customary meaning of average molecular weight in connection with the polymer. When a numerical value or range is specified for an "average molecular weight" of a polymer, it should be understood as satisfied if the polymer has either the number average molecular weight or weight average molecular weight within the specified value or range, unless otherwise specified or it is contrary to the customary meaning of average molecular weight in connection with the polymer. In some embodiments, the "average molecular weight" refers to number average molecular weight, or $M_n$. In some embodiments, the "average molecular weight" refers to weight average molecular weight, or $M_w$.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a gel formulation of the present disclosure to a subject in need of such treatment.

The term "therapeutically effective amount," as used herein, refers to that amount of a therapeutic agent (e.g., the gel formulation of the present disclosure) sufficient to result in amelioration of one or more symptoms of a disorder or condition (e.g., cold sores), or prevent appearance or advancement of a disorder or condition, or cause regression of or cure from the disorder or condition.

The term "subject" (alternatively referred to herein as "patient") as used herein, refers to an animal, preferably a mammal, most preferably a human, who has been the object of treatment, observation or experiment. In any of the embodiments described herein, the subject can be a human.

EXAMPLES

The following examples illustrate the present disclosure without limitation. Acyclovir used in the studies was obtained from Hetero Drugs. Materials with appropriate grade can be commercially purchased. The following shows exemplary sources of representative materials used herein.

Example 1. Solubility and Stability of Acyclovir in Topical Excipients

This Example studies the solubility and stability of acyclovir in various topical excipients. Table 1 and Table 2 below indicate the various excipients that solubility was tested in and stability of acyclovir in these excipients, respectively.

TABLE 1

Saturated solubility of acyclovir (% w/w) in excipients suitable for topical application, determined by HPLC (n = 3).

| Excipient | Saturated solubility of Acyclovir (% w/w) |
|---|---|
| Ethanol | Below LOQ (i.e., below 0.03 μg/ml) |
| Isopropyl alcohol | Below LOQ |
| Benzyl alcohol | 0.05 (0.04-0.05) |
| Buffer pH4 | 0.10 (0.10-0.10) |
| Buffer pH5 | 0.10 (0.09-0.10) |
| Buffer pH6 | 0.10 (0.09-0.10) |
| Buffer pH7 | 0.10 (0.10-0.10) |
| PEG 400 | 0.09 (0.09-0.09) |
| Super refined PEG400 | 0.09 (0.08-0.09) |
| Phenoxyethanol | 0.20 (0.06-0.29) |
| DMI | Below LOQ |
| Oleyl Alcohol | Below LOQ |
| Propylene glycol | 0.25 (0.24-0.26) |
| Transcutol P | 0.01 (0.01-0.01) |
| Transcutol HP | 0.02 (0.01-0.03) |
| Castor Oil | Below LOQ |
| Diisopropyl adipate | Below LOQ |

| Material | Batch/Lot Number | Grade | Supplier |
|---|---|---|---|
| Acetonitrile | 1900707, 1901743, 1904154, 1990245, 1994099 19C064020 | HPLC | Fisher VWR |
| | 1911073 | LCMS | Fisher |
| Carbopol 980 | 0102136164, 0102136175 | Pharma | Lubrizol |
| Crodamol GTCC | 0001182278, 0001323603 | Ph Eur, USP/NF | Croda |
| Dietyl ether | H1115 | HPLC | Honeywell |
| Dimethyl sulfoxide | 1710280, 1862997, 1867992 19E064118 | Analytical Ph Eur | Fisher VWR |
| Hexane | 1685354 | HPLC | Fisher |
| Hydroxymethyl cellulose | R0115 | Pharma | Ashland |
| Hydroxymethyl cellulose | 188495 | | |
| Isopropyl alcohol | 19A164614 | HPLC | VWR |
| Methanol | 1882060, 1991615, 1996473 19C194008 | HPLC | Fisher VWR |
| | 1996019 | LCMS | Fisher |
| PEG 400 | K491100903, K51372503 | Ph Eur, JP | Merck |
| Phenoxyethanol | 17F294108, 18A154114 | Ph Eur | VWR |
| Phosphoric acid | SZBG3140H | Analytical, 85-88% | Honeywell |
| | STBH9987, SZBG1110V | Ph Eur | Sigma |
| Potassium phosphate | A0381518 | HPLC | Acros |
| Propylene glycol | K49089078, K48209478 | Ph Eur, BP, USP | Merck |
| Propylene glycol (super refined) | 0001211510 | Ph Eur | Croda |
| Sepineo P600 | 180427011450 | Pharma | Seppic |
| Sodium hydroxide | B1627282 | Ph Eur, BP, FCC, JP, NF, E524 | Merck |
| Transcutol HP | 162775160563 | Ph Eur, USP/NF | Gattefosse |
| Water | In house | 18.2 MΩ.cm | Milli Q |
| | 18L139001 | HPLC | VWR |
| | 13LLP221, 13NAP011, 13NEP083 | Ph Eur | Fresenius kabi |

TABLE 1-continued

Saturated solubility of acyclovir (% w/w) in excipients suitable for topical application, determined by HPLC (n = 3).

| Excipient | Saturated solubility of Acyclovir (% w/w) |
|---|---|
| Isopropyl myristate | Below LOQ |
| Miglyol 810 | Below LOQ |
| Mineral Oil | Below LOQ |
| Propylene glycol dicapylate | Below LOQ |
| Hexylene Glycol | Below LOQ |
| DMSO | 8.59 (6.74-9.61) |
| Buffer pH 7 with 15% w/w Tween 80 | 0.09 (0.09-0.10) |
| Buffer pH 7 with 4.15% w/w Brij S20 | 0.09 (0.09-0.09) |
| Buffer pH 7 with 1% w/w Kolliphor P407 | 0.09 (0.09-0.09) |
| Buffer pH 7 with 1.5% w/w gamma cyclodextrin | 0.09 (0.09-0.09) |
| Buffer pH 5 with 15% w/w Tween 80 | 0.09 (0.09-0.09) |
| SS1 | 0.15 (0.14-0.15) |
| SS2 | 0.21 (0.21-0.21) |
| 1.5% w/w Gamma cyclodextrin | 0.14 (0.14-0.14) |
| HP beta cyclodextrin (1.5% in water) | 0.15 (0.15-0.15) |
| SBE beta cyclodextrin (1.5% in water) | 0.15 (0.15-0.15) |
| Capmul MCM (10% in ethanol) | 0.02 (0.02-0.02) |
| Capmul PG-12 (10% in ethanol) | 0.02 (0.02-0.02) |
| Labrasol | Below LOQ |
| Acconon MC8 | Below LOQ |
| Triacetin | Below LOQ |
| Triethyl citrate (1% in water) | 0.15 (0.15-0.15) |
| NMP | 2.53 (2.51-2.55) |
| Propylene glycol diacetate | Below LOQ |
| Water based urea solution (10% w/w) | 0.13 (0.11-0.14) |
| 10% DMSO in water | 0.17 (0.17-0.17) |

Table 2 shows stability of acyclovir in some excipients following storage for 2 weeks at 25° C. and 40° C.

TABLE 2

Percentage recovery of acyclovir as a percentage of the theoretical concentration from excipients at t = 0 and following storage for t = 2 weeks at 25 and 40° C. (n = 3)

| | | Percentage recovery of acyclovir following t = 2 week storage | |
|---|---|---|---|
| Excipient | T = 0 | 25° C. | 40° C. |
| Buffer pH 4 | 105.23 (104.73-105.49) | 103.57 (101.71-105.75) | 105.37 (104.80-105.84) |
| Buffer pH 5 | 101.90 (101.73-102.08) | 99.69 (99.10-100.27)* | 99.66 (99.36-100.17) |
| Buffer pH 6 | 104.96 (104.51-105.30) | 102.83 (101.68-103.45) | 102.69 (102.08-103.00) |
| Buffer pH 7 | 104.85 (104.47-105.04) | 101.71 (101.51-101.83) | 102.25 (102.02-102.37) |
| DMSO | 101.39 (101.04-101.63) | 101.21 (100.86-101.57) | 101.31 (101.28-101.34)* |
| PEG 400 | 104.61 (104.34-104.76) | 101.66 (101.52-101.84) | 99.57 (98.87-100.08) |
| Super refined PEG 400 | 102.92 (102.44-103.85) | 98.16 (97.82-98.38) | 91.71 (85.11-95.37) |
| Propylene glycol | 101.74 (101.31-102.40) | 98.38 (97.67-98.74) | 98.07 (97.85-98.37) |
| Phenoxy ethanol | 105.89 (105.07-107.40) | 104.15 (103.77-104.57) | 103.60 (102.67-104.31) |
| Buffer pH 7 with 15% w/w Tween 80 | 107.67 (107.28-108.01) | 108.02 (107.76-108.55) | 107.21 (106.34-107.80) |

Example 2. Preparation of Cream, Aqueous, and Non-Aqueous Acyclovir Formulations In this Example, a range of formulations were prepared and placed on stability to determine which of the formulations were the most stable. Additionally, each formulation was evaluated for the following factors (1) chemical and physical stability, (2) pH, (3) drug load, (4) aesthetics, (5) acceptable amounts of approved excipients, and (6) presence of antioxidants and/or preservatives. The formulations that were evaluated are given in Table 3 (cream and emulsified gel formulations), Table 4 (aqueous based formulations) and Table 5 (Non-aqueous based formulations) below.

The apparent pH and macroscopic appearance of most of these formulations remained consistent on short term stability (2 weeks at 25 and 40° C.). Based on all the above factors the formulation CR05, EG03, AG18, AG20 and NA14 were selected as candidates for performance testing.

TABLE 3

Composition of cream and emulsified gel formulations

| | Composition of active cream and emulsified gel formulations (% w/w) | | |
|---|---|---|---|
| Ingredient | CR05 | EG01 | EG03 |
| Acyclovir (non-micronized) | 0.157 | 0.173 | 0.40* |
| Water | 49.94 | 30.19 | 29.97 |
| PEG 400 | 13.90 | 19.63 | 19.63 |
| Phenoxyethanol | 1.00 | 1.00 | 1.00 |
| Propylene glycol | — | 10.00 | 10.00 |
| Transcutol ® HP | 15.00 | 15.00 | 15.00 |
| Sepineo ™ P600 | — | 4.00 | 4.00 |
| Dimethicone 350 | 1.00 | — | — |
| Crodamol ™ GTCC | 5.00 | 10.00 | 10.00 |
| Cyclomethicone 5NF | 8.00 | — | — |
| Beeswax (white wax) | 0.50 | — | — |
| Cetostearyl alcohol | 0.50 | — | — |
| Brij S2 | 3.47 | — | — |
| Brij S20 | 1.53 | — | — |
| 0.2M NaOH | — | pH 6-6.5 | pH 6-6.5 |
| 2nd Addition of water | — | Q.S 100% | Q.S 100% |
| Total | 100.00 | 100.00 | 100.00 |

CR = cream;
EG = emulsified gel;
NaOH = sodium hydroxide;
NF = national formulary;
PEG = polyethylene glycol
*EG03 contained the drug in suspension;
(—) not included

TABLE 4

Composition of aqueous based acyclovir formulations

Composition of active aqueous gel formulations (% w/w)

| Ingredient | AG02 | AG11 | AG14 | AG15 | AG16 | AG17 | AG18 | AG19 | AG20 |
|---|---|---|---|---|---|---|---|---|---|
| Acyclovir (non-micronized) | 0.167 | 0.188 | 0.157 | 0.151 | 0.188 | 0.173 | 0.151 | 0.197 | 0.188 |
| Water | 38.83 | 48.71 | 61.55 | 47.85 | 48.96 | 39.03 | 67.85 | 60.55 | 38.96 |
| DMSO | 5.00 | — | — | — | — | — | — | — | — |
| PEG 400 | 29.90 | — | 17.50 | 40.00 | — | 23.80 | — | 17.50 | — |
| Sodium metabisulfite | 0.10 | 0.10 | — | — | 0.10 | — | — | — | 0.10 |
| Phenoxyethanol | — | — | 1.00 | 1.00 | — | 1.00 | 1.00 | — | — |
| Benzyl alcohol | — | — | — | — | — | — | — | 2.00 | — |
| Propylene glycol | — | 20.00 | — | — | 20.00 | 10.00 | 20.00 | — | 20.00 |
| Transcutol ® HP | 15.00 | 15.00 | 18.75 | — | 15.00 | 25.00 | — | 18.75 | 15.00 |
| Glycerol | — | 15.00 | — | — | 15.00 | — | — | — | 15.00 |
| Carbopol ® 980 | 1.00 | — | — | 1.00 | — | — | 1.00 | — | 0.75 |
| HEC | — | 1.00 | 1.00 | — | 0.75 | 1.00 | — | 1.00 | — |
| 0.2M NaOH | pH 6-6.50 | — | — | pH 6-6.50 | — | — | pH 6-6.50 | — | pH 5-6.0 |
| 2$^{nd}$ Addition of Water | Q.S 100% | — | — | Q.S 100% | — | — | Q.S 100% | — | Q.S 100% |
| Total | 100.00 | 100.00 | 100.00 | 100.00 | 100.00 | 100.00 | 100.00 | 100.00 | 100.00 |

DMSO = dimethyl sulfoxide;
HEC = hydroxyethyl cellulose;
NaOH = sodium hydroxide;
PEG = polyethylene glycol
(—) not included

TABLE 5

Composition of non-aqueous formulations

Composition of active non-aqueous gel formulations (% w/w)

| Ingredient Formulation name | NA14 | NA15 | NA17 | NA18 | NA19 |
|---|---|---|---|---|---|
| Acyclovir (micronized) | 0.157 | 0.298 | 0.100 | 0.103 | 0.100 |
| DMSO | 10.00 | — | — | — | — |
| PEG 400 | 53.84 | 63.20 | 63.80 | 50.90 | 63.90 |
| BHT | — | — | 0.10 | — | — |
| Propylene glycol | 10.00 | 20.00 | 10.00 | — | 10.00 |
| Transcutol ® HP | 25.00 | — | 25.00 | 25.00 | 25.00 |
| Diisopropyl adipate | — | — | — | 10.00 | — |
| Glycerol | — | 15.00 | — | 10.00 | — |
| HPC-JF | — | — | — | 4.00 | — |
| HPC-MF | 1.00 | — | 1.00 | — | 1.00 |
| HPC-GF | — | 1.50 | — | — | — |
| Total | 100.00 | 100.00 | 100.00 | 100.00 | 100.00 |

BHT = butylated hydroxytoluene;
DMSO = dimethyl sulfoxide;
HPC = hydroxypropyl cellulose;
NA = non-aqueous;
PEG = polyethylene glycol
Note:
JF, MF, and GF designations for HPC indicate viscosity type (M > G > J from highest to lowest viscosity) and market segment (F = pharmaceutical)
(—) not included Example 3. Preparation and In Vitro Testing of Aqueous and Non-Aqueous Formulation Based on the results from Example 2, a cream formulation (CR05), an emulsified gel formulation (EG03), two aqueous gel formulations (AG18 and AG20) and an non-aqueous gel formulation (NA14) were prepared and selected for in vitro release testing (IVRT) and in vitro permeation testing (IVPT). Table 3-5 shows the compositions of these five formulations.

Example 3A. In Vitro Release Testing (IVRT)

Prior to doing the IVRT studies experiments were performed to identify the best membrane to use as well and the receiver solution, and determination of appropriate sampling time points. Based on these studies, the following conditions were used in the IVRT testing:
Replicates: n=6
Dose: 300 mg
Receiver fluid investigated: 10% v/v PEG 400 in Citrate phosphate buffer pH 4
Synthetic membrane assessed: PTFE
Time points: 2, 4, 6, 24, 26 and 28 h The release rate of acyclovir from the various formulations is given in Table 6. Zovirax® Cream 5% was used as a reference control. It was determined that the Suspension formulations (Zovirax® Cream 5% and EG03) had the greatest release rate of acyclovir into the receiver fluid. Of the formulations where the drug was in solution, CR05 had the highest rate of release, followed by NA14. There were minimal amounts (<4 μg/cm$^2$ at the final timepoint of t=28 hours) of acyclovir detected in the receiver fluid for both aqueous gel formulations AG18 and AG20.

TABLE 6

Rate of release for formulations from t = 4 – 28 h.

| Formulation | Concentration of acyclovir (% w/w) | Rate of release (μg/cm$^2$/h) |
|---|---|---|
| CR05 | 0.157 | 14.19 |
| EG03 | 0.400* | 43.01 |
| AG20 | 0.188 | ND |
| NA14 | 0.157 | 0.74 |
| AG18 | 0.151 | ND |
| Zovirax ® | 5.000* | 156.94 |

*Contains drug in suspension

Example 3B. In Vitro Permeation Testing (IVPT)

Prior to doing the IVPT studies experiments were performed to identify the receiver solution, and determination of appropriate sampling time points. Based on these studies, the following conditions were used in the IVPT testing:
Replicate: 3-5 donors
Dose: 6-7 mg
Receiver fluid investigated: citrate phosphate buffer, pH 4
Tissue assessed: human abdominal skin (dermatomed)
Time points: 0, 1, 2, 4, 6, 24, 30 and 48 h The permeation rates for each of the formulation is shown in FIG. 1. As can be seen from FIG. 1, Formulations EG03 and NA14 were found to have a cumulative amount of acyclovir at 24 hours about the same as that observed for Zovirax® Cream 5%. FIG. 2 further shows the amount of acyclovir recovered from epidermis and dermis as a Percentage of the Applied Dose at 28 hours post application. As a general trend, the tested formulations delivered acyclovir in greater amounts to the epidermis than the dermis, with the exception of NA14. The ranking of the formulations (highest to lowest) in terms of the percentage of the applied dose recovered from the epidermis was: AG18>AG20>CR05>EG03>U.S. Zovirax® Cream 5%>NA14.

Example 4. Preparation of Aqueous Gel and Emulsified Gel Formulations

Based on the performance of EG03 and NA14 in the IVRT and IVPT experiments, these two formulations were optimized, using Design of Experiments (DoE), for the excipients of (1) water, (2) PEG400, (3) propylene glycol, and (4) Transcutol® HP. The purpose of the DoE was to determine the formulation composition with the maximum acyclovir solubility. Based on the results of this DoE the formulation in Table 7 were manufactured and placed on stability.

TABLE 7

Optimized acyclovir formulation that are being evaluated for stability

| | Theoretical composition (% w/w) | | | | |
|---|---|---|---|---|---|
| | Aqueous gels | | | Emulsified gels | |
| Formulation | AG21 | AG23 | AG26 | EG04 | EG09 |
| Acyclovir | 0.203 | 0.202 | 0.204 | 0.175 | 0.180 |
| Water | 29.297 | 29.448 | 29.296 | 24.169 | 24.164 |
| PEG 400 | 9.100 | 11.687 | 29.500 | 7.813 | 25.328 |
| Phenoxyethanol | 1.000 | 1.000 | 1.000 | 1.000 | 1.000 |
| SR Propylene glycol | 0.000 | 19.060 | 8.441 | 0.000 | 7.247 |
| Transcutol® HP | 49.900 | 28.253 | 21.059 | 42.843 | 18.081 |
| Carbopol® 980 | 0.500 | 0.350 | 0.500 | — | — |
| Sepineo™ P600 | — | — | — | 4.000 | 4.000 |
| Crodamol™ GTCC | — | — | — | 10.000 | 10.000 |
| 0.2M NaOH | | | pH 6-6.5 | | |
| 2nd Addition of water* | Q.S 100% | Q.S 100% | Q.S 100% | Q.S 100% | Q.S 100% |
| Total | 100.000 | 100.000 | 100.000 | 100.000 | 100.000 |

The 5 formulations presented in Table 7 were selected for inclusion on short-term stability with testing performed at t=0 and following 2 and 4 weeks at 25 and 40° C. At each timepoint, the following parameters were assessed: Acyclovir content and purity, apparent pH, macroscopic observations, and microscopic observations.

The acyclovir peak purities were consistent (>99.5%) for all formulations at t=0 and following 2 and 4 weeks at 25 and 40° C.

The acyclovir recoveries for AG21, AG23, AG26 and EG04 were good (between 95% and 105%) and consistent for all formulations at t=0 and following storage at 25 and 40° C. for 2 and 4 weeks. The mean recovery for EG09 was low at t=0 (91.53% w/w); however, recovery results at the 2 and 4 week timepoints were between 95% and 105% and so it is likely that the t=0 results were due to incomplete extraction, as the extraction procedure has not been optimized for formulations at the time of this example.

The formulations designed had apparent pH readings which ranged between 5.5 and 6.5 pH units at t=0. There was no notable change (>0.5 pH units) from t=0 for any formulations assessed following storage up to 4 weeks at 25 and 40° C.

At t=0 all the aqueous gels were colorless and clear with low or medium viscosity and the emulsified gels were off-white and opaque with high viscosity. Following storage for 2 weeks at 25 and 40° C., there was no change from t=0 in any formulation except for AG21 0.20% w/w where an increase in viscosity (low to medium) was observed in the samples stored at both 25 and 40° C.

Following 4 weeks storage at 25 and 40° C., the AG21 active maintained the medium viscosity observed at the 2-week timepoint. In addition, the AG23 placebo was observed to have increased viscosity (low to medium) at this timepoint at both storage temperatures. No obvious changes from t=0 were seen in the other formulations assessed.

Following 2 weeks storage at 25 and 40° C. there were no changes in the majority of the formulations, however gelling agent was observed in AG21 at 40° C. (which is believed to be due to processing) and changes in droplet shape were observed in EG04 placebo at 25° C. and EG09 0.18% w/w at 40° C.

At the 4-week timepoint irregular droplet size was observed for EG04 placebo and EG09 active and placebo. The same trend was seen at 2-8° C. for EG09 active and placebo but in EG04 active and placebo the dispersed phase was non-uniform and irregular droplet size was observed There were no obvious changes from t=0 noted for the other formulations.

Each of these seven formulations is considered as having acceptable physical stability profile with no physical stability issues observed at storage and accelerated conditions.

Table 8 shows the differences between the U.S. FDA approved 5% Zovirax® Cream 5% (see e.g., Zovirax® Cream 5% Prescribing Information, rev. 2014) and selected gel formulations of this disclosure in which contain Water, PEG400, Propylene Glycol, and Transcutol® HP.

TABLE 8

Ingredients of gel formulation compared to Zovirax® Cream 5% Formulations

| Gel Formulation Components | Zovirax® Cream 5% Components |
|---|---|
| Acyclovir | Acyclovir |
| Water | Water |
| PEG 400 | Cetostearyl alcohol |
| Phenoxyethanol | Mineral oil |
| SR Propylene glycol | Poloxamer 407 |

TABLE 8-continued

Ingredients of gel formulation compared to Zovirax ® Cream 5% Formulations

| Gel Formulation Components | Zovirax ® Cream 5% Components |
|---|---|
| Transcutol ® HP | Propylene glycol |
| Carbopol ® 980 | Sodium lauryl sulfate |
| Sepineo ™ P600 | White petrolatum |
| Crodamol ™ GTCC | |
| Sodium hydroxide | |

Example 5. Additional In Vitro Permeation and Penetration Test (IVPT)

This Example was designed to test in vitro permeations and penetration of several formulations herein containing acyclovir compared to the marketed formulation, Zovirax® Cream 5%.

The formulations tested are described in Table 9A below:

TABLE 9A

Test Formulation Summary

| Name | Formulation Type | FIGURE Label | API Concentration (% w/w) |
|---|---|---|---|
| Zovirax | Cream* | Zovirax (5%) | 5% |
| AG23-HC | Aqueous Gel* | AG23 (5%) | 5% |
| EG04-HC | Emulsified Gel* | EG04 (5%) | 5% |
| EG03 | Emulsified Gel | EG03 (0.4%) | 0.4% |
| AG21 | Aqueous Gel | AG21 (0.2%) | 0.2% |
| AG23 | Aqueous Gel | AG23 (0.2%) | 0.2% |
| AG26 | Aqueous Gel | AG26 (0.2%) | 0.2% |
| EG04 | Emulsified Gel | EG04 (0.18%) | 0.18% |
| EG09 | Emulsified Gel | EG09 (0.18%) | 0.18% |
| NA14 | Non-Aqueous Gel | NA14 (0.16%) | 0.16% |

*API in suspension. Remaining formulations contain API in solution.

The formulation details of AG21, AG23, AG26, EG03, EG04, EG09, and NA14 are described herein. The high concentration formulations AG23-HC and EG04-HC have the following ingredients shown in Table 9B:

TABLE 9B

Compositions of AG23-HC and EG04-HC

| | Composition (% vv/w) | |
|---|---|---|
| Excipients | AG23-HC | EG04-HC |
| Acyclovir | 5.00 | 5.00 |
| Water | 27.53 | 22.22 |
| PEG 400 | 11.12 | 7.37 |
| Phenoxyethanol | 1.00 | 1.00 |
| Propylene glycol | 18.13 | |
| Transcutol ® HP | 26.87 | 42.84 |
| Carbopol ® 980 | 0.35 | — |
| Sepineol ™ P600 | — | 4.00 |
| Crodamol ™ GTCC | — | 10.00 |
| 0.2M NaOH | To pH 6-6.5 | To pH 6-6.5 |
| Water (2$^{nd}$ addition) | Q.S 100% | Q.S 100% |
| Total | 100.00 | 100.00 |

The in vitro permeation and penetration investigation was performed using the 10 formulations in Table 9A. A summary of the experimental conditions is shown in Table 9C.

TABLE 9C

Experimental conditions for the in vitro permeation and penetration experiments.

| Setup | Full Scale |
|---|---|
| Skin type | Dermatomed human abdominal skin from elective surgery |
| Thickness (μm) | 500 ± 50 |
| No. skin donors | 1 |
| Receptor solution | Citrate phosphate buffer pH 4.0 |
| No. formulations | Ten |
| No. replicates | 7 |
| No. skin blanks | 1 |
| Dose amount | 10 mg/cm$^2$ |
| MedFlux Cell Type/Flow Rate | Low velocity/6 μL/min |
| RS collection times | 0.5, 1, 2, 3, 6, 9, 12, 15, and 19 hr |
| Skin Tissue Procedures | |
| Extraction Fluid | 90:10 v/v ethanol:water |
| Surface of skin | discard |
| Stratum corneum | discard |
| Separate dermis and epidermis? | Yes (retain for analysis) |
| Epidermis extraction procedure | retain for analysis |
| Dermis extraction procedure | retain for analysis |

The data was interpreted as follows:

The concentration of acyclovir detected in the receptor solution and skin layers was quantified using a calibration range optimized for the analysis of the samples generated during the in vitro skin permeation and penetration experiments.

Any outliers were rejected according to internal procedures.

The amount of acyclovir recovered from the epidermis and dermis was calculated at the conclusion of the run. Means and standard deviations were calculated and reported. Data was log transformed and statistically compared using a one-way with Tukey HSD analysis.

The cumulative amount per cm$^2$ of acyclovir permeated into the receptor solution was calculated from drug concentrations measured in the receptor solution over time. The cumulative amount per cm$^2$ of acyclovir at the final timepoint was calculated for each replicate. Means and standard deviations were calculated and reported. Data was log transformed and statistically compared using a one-way ANOVA with Tukey HSD.

The percent of applied dose was calculated by dividing the total amount of API recovered from the skin layers and receptor solution by the amount of API dosed onto the skin, multiplied by 100.

Results:

The mean amount (ng) of acyclovir recovered from epidermis and dermis is presented in Table 10A. The mean percent applied dose of acyclovir recovered from the epidermis and dermis can be found in Table 10B.

As a general trend, AG23-HC (5%) and the comparator Zovirax® delivered higher amounts of acyclovir to the epidermis after 19 h, although no significant differences were noted between the two. However, when considering the percent of applied dose, EG04 (0.18%) and AG23 (0.2%) delivered 5- and 4-fold greater (p<0.05) amounts of acyclovir to the epidermis compared to Zovirax®.

As a general trend, AG23-HC (5%), Zovirax®, and EG04-HC (5%) delivered the highest amount of acyclovir to the dermis after 19 h, although no significant differences were noted between the three formulations. When considering the percent applied dose, EG04 (0.18%), AG21 (0.2%), AG23 (0.2%), AG26 (0.2%), and NA14 (0.16%)

delivered greater (3- to 7-fold) amounts (p<0.05) of acyclovir to the dermis compared to Zovirax®.

TABLE 10A

Mean cumulative amount (ng) of acyclovir recovered from epidermis and dermis 24 hours post formulation application (presented as mean and standard deviation).

| Formulation | Dermis (ng) | | | Epidermis (ng) | | |
|---|---|---|---|---|---|---|
| | N | Mean | Std Dev | N | Mean | Std Dev |
| AG23-HC (5%) | 7 | 4000 | 1665 | 6 | 22832 | 11293 |
| Zovirax (5%) | 7 | 2993 | 1944 | 7 | 7446 | 2989 |
| EG04-HC (5%) | 7 | 1906 | 1323 | 7 | 6070 | 5272 |
| AG23 (0.2%) | 7 | 410 | 118 | 7 | 1536 | 1032 |
| EG04 (0.18%) | 6 | 774 | 503 | 5 | 1120 | 243 |
| EG03 (0.4%) | 6 | 345 | 146 | 7 | 919 | 681 |
| AG21 (0.2%) | 7 | 447 | 180 | 7 | 778 | 307 |
| AG26 (0.2%) | 7 | 389 | 95 | 7 | 546 | 278 |
| EG09 (0.18%) | 7 | 149 | 88 | 7 | 207 | 110 |
| NA14 (0.16%) | 6 | 355 | 201 | 6 | 225 | 107 |
| Blank | 1 | 0 | . | 1 | 0 | . |

TABLE 10B

Mean cumulative amount (percent applied dose) of acyclovir recovered from epidermis and dermis 24 hours post formulation application (presented as mean and standard deviation).

| Formulation | Dermis (% Applied Dose) | | | Epidermis (% Applied Dose) | | |
|---|---|---|---|---|---|---|
| | N | Mean | Std Dev | N | Mean | Std Dev |
| AG23-HC (5%) | 7 | 0.78% | 0.33% | 6* | 4.49% | 2.31% |
| Zovirax (5%) | 7 | 0.60% | 0.39% | 7 | 1.49% | 0.62% |
| EG04-HC (5%) | 7 | 0.38% | 0.26% | 7 | 1.21% | 1.05% |
| AG23 (0.2%) | 7 | 2.03% | 0.64% | 7 | 7.59% | 5.14% |
| EG04 (0.18%) | 6† | 4.33% | 2.80% | 5*† | 6.19% | 1.15% |
| EG03 (0.4%) | 6 | 0.86% | 0.35% | 7 | 2.28% | 1.65% |
| AG21 (0.2%) | 7 | 2.21% | 0.93% | 7 | 3.86% | 1.57% |
| AG26 (0.2%) | 7 | 1.96% | 0.44% | 7 | 2.75% | 1.38% |
| EG09 (0.18%) | 7 | 0.81% | 0.47% | 7 | 1.13% | 0.59% |
| NA14 (0.16%) | 6† | 2.21% | 1.25% | 6† | 1.40% | 0.67% |

*Dixon outlier removed
†Due to technical issues, some receptor solution samples were not collected, and results are therefore not reportable.

The amount of acyclovir which permeated across the skin into the receptor solution over 19 h, following the application of the test formulations to the surface of the tissue is shown in FIG. 3 and described in Table 10C. In addition, the amount (percent applied dose) of acyclovir permeating through the 1 cm$^2$ skin dosing area (i.e. drug detected in receptor solution at 0.5, 1 and 2 h) following application of formulations is also presented in FIG. 3 and described in Table 10D.

As a trend, NA14 (0.16% w/w) delivered approximately 400 ng of acyclovir to the receptor solution after 19 hours (compared to Zovirax® which delivered 45 ng), although no significant differences were noted among the formulations, with the only exception being the EG04-HC (5%) suspension, which delivered the lowest amount of acyclovir by 10-fold (p<0.05).

After 2 hours (typical re-application time of Zovirax®) AG21 (0.2%), EG04 (0.18%), and NA14 showed a higher trend of cumulative delivery of acyclovir, although no differences were detected compared to Zovirax®. When considering the percent of applied dose, EG04 (0.18%), AG21 (0.2%), NA14 (0.16%), AG23 (0.2%), and AG26 (0.2%) delivered greater (11- to 120-fold) amounts of acyclovir (p<0.05) to the receptor solution compared to Zovirax®.

TABLE 10C

Mean cumulative amount (ng/cm$^2$) of acyclovir permeated through the 1 cm$^2$ skin dosing area into citrate/phosphate buffer pH 4.0 19 hours following application of 10 formulations. Single skin donor; n = 4-7.

| Formulation | Cumulative Amount API (ng/cm$^2$) | | |
|---|---|---|---|
| | N | Mean | Std Dev |
| NA14 (0.16%) | 4*† | 401.24 | 442.74 |
| AG21 (0.2%) | 6* | 237.07 | 151.24 |
| EG04 (0.18%) | 6† | 190.86 | 143.24 |
| AG23-HC (5%) | 7 | 144.85 | 133.28 |
| AG26 (0.2%) | 7 | 94.98 | 96.57 |
| AG23 (0.2%) | 7 | 81.40 | 79.96 |
| EG09 (0.18%) | 5*† | 58.57 | 54.56 |
| Zovirax (5%) | 6* | 45.05 | 33.33 |
| EG03 (0.4%) | 6* | 10.68 | 6.27 |
| EG04-HC (5%) | 5*† | 1.21 | 2.39 |
| Blank | 2 | 0.02 | 0.02 |

*Dixon outlier removed
†Due to technical issues, some receptor solution samples were not collected, and results are therefore not reportable.

TABLE 10D

Mean cumulative amount (expressed as percent applied dose) of acyclovir permeating through the 1 cm$^2$ skin dosing area (i.e. drug detected in receptor solution at 0.5, 1 and 2 hr) following application of formulations (n = 4-7).

| | | % applied dose | | | | | |
|---|---|---|---|---|---|---|---|
| | | 0.5 hr | | 1 hr | | 2 hr | |
| Formulation | N | Mean | Standard Deviation | Mean | Standard Deviation | Mean | Standard Deviation |
| NA14 (0.16%) | 4*† | 0.0163 | 0.0001 | 0.0616 | 0.0001 | 0.1508 | 0.0011 |
| AG21 (0.2%) | 6* | 0.0293 | 0.0003 | 0.0760 | 0.0007 | 0.1556 | 0.0012 |
| EG04 (0.18%) | 6† | 0.0387 | 0.0007 | 0.1306 | 0.0021 | 0.2810 | 0.0039 |
| AG23-HC (5%) | 7 | 0.00107 | 0.0000 | 0.0034 | 0.0000 | 0.0064 | 0.0001 |
| AG26 (0.2%) | 7 | 0.00137 | 0.0000 | 0.0087 | 0.0000 | 0.0260 | 0.0002 |
| AG23 (0.2%) | 7 | 0.00797 | 0.0001 | 0.0304 | 0.0003 | 0.0710 | 0.0006 |
| EG09 (0.18%) | 5*† | 0.00410 | 0.0000 | 0.0183 | 0.0002 | 0.0433 | 0.0004 |

TABLE 10D-continued

Mean cumulative amount (expressed as percent applied dose) of acyclovir permeating through the 1 cm² skin dosing area (i.e. drug detected in receptor solution at 0.5, 1 and 2 hr) following application of formulations (n = 4-7).

| | | % applied dose | | | | | |
|---|---|---|---|---|---|---|---|
| | | 0.5 hr | | 1 hr | | 2 hr | |
| Formulation | N | Mean | Standard Deviation | Mean | Standard Deviation | Mean | Standard Deviation |
| Zovirax (5%) | 6* | 0.00076 | 0.0000 | 0.0015 | 0.0000 | 0.0023 | 0.0000 |
| EG03 (0.4%) | 6* | 0.00217 | 0.0000 | 0.0068 | 0.0001 | 0.0103 | 0.0001 |
| EG04-HC (5%) | 5*† | 0.00002 | 0.0000 | 0.0001 | 0.0000 | 0.0001 | 0.0000 |

*Dixon outlier removed
†Due to technical issues, some receptor solution samples were not collected, and results are therefore not reportable.

As a trend, NA14 delivered approximately 400 ng of acyclovir to the receptor solution after 19 hours (compared to Zovirax® which delivered 45 ng), although no significant differences were noted among the formulations applied, with the only exception being the EG04-HC 5% suspension, which delivered the lowest amount of acyclovir by 10-fold ($p<0.05$). Even at a much lower acyclovir concentrations, after 2 hours (typical re-application time of Zovirax®), AG21 (0.2%), EG04 (0.18%), and NA14 showed a higher trend of cumulative delivery of acyclovir, although no differences were detected compared to Zovirax®. When considering the percent of applied dose, EG04 (0.18%), AG21 (0.2%), NA14 (0.16%), AG23 (0.2%), and AG26 (0.2%) delivered greater (11- to 120-fold) amounts of acyclovir ($p<0.05$) to the receptor solution compared to Zovirax®.

Example 6. Scale-Up Preparation of Selected Formulations

The active formulations detailed in Table 11 were manufactured on a 30 g scale to supply the pig open flow micro perfusion study herein. Placebo formulations were not supplied for the micro perfusion study.

Preparation of Aqueous Gel Formulations:

The aqueous gels (AG21, AG21-placebo, AG23, and AG23-placebo) were manufactured according to the procedure below:
(i) PEG400, phenoxyethanol, Transcutol® HP and propylene glycol (for AG23 and AG23-placebo), were weighed into a suitably sized vessel, vortexed briefly and mixed until clear.
(ii) For AG21 and AG23 only: Acyclovir was added to the vessel from Step (i) and stirred at approximately 900 rpm with a magnetic stirrer bar until visibly dissolved.
(iii) Water (90% of total) was added to the vessel from Step (ii) for AG21 and AG23 or Step (i) for placebos.
(iv) Carbopol® 980 was weighed into a suitably sized vessel and slowly added to the vessel from Step (iii) whilst stirring at 1500 rpm in order to create a vortex.
(v) The formulation from Step (iv) was then stirred until the gelling agent was fully hydrated and pH adjusted with 0.2M NaOH to pH 6-6.5.
(vi) Water (2$^{nd}$ addition) was added to the vessel from Step (v) to make up to 100% and the formulation was stirred for 30 minutes to ensure homogeneity before a final pH check was performed.

Preparation of Emulsified Gel Formulations:

The emulsified gel (EG04 and EG04-placebo) were manufactured according to the procedure below:
(i) PEG400, phenoxyethanol, Transcutol® HP, were weighed into a suitably sized vessel, vortexed briefly and mixed until clear.
(ii) For the EG04 only: Acyclovir was added to the vessel from Step (i) and stirred at approximately 900 rpm with a magnetic stirrer bar until visibly dissolved.
(iii) Water (90% of total) was added to the vessel from Step (ii) for EG04 or Step (i) for EG04-placebo.
(iv) Into a separate vessel Sepineo™ P600 and Crodamol™ GTCC were weighed and stirred at approximately 500 rpm with a magnetic stirrer bar until the Sepineo™ P600 was fully dispersed.
(v) The oil phase from Step (iv) was added to the aqueous phase from Step (iii) and stirred at 500-900 rpm until a viscous, white formulation was formed. The formulation was then stirred manually using a stainless-steel spatula until visibly homogenous.
(vi) The formulation from Step (v) was pH adjusted with 0.2M NaOH to pH 6-6.5.
(vii) Water (2$^{nd}$ addition) was added to the vessel from Step (vi) to make up to 100% and the formulation was stirred for 30 minutes to ensure homogeneity.

Preparation of Non-Aqueous Gel Formulations:

The non-aqueous gel (NA14 and NA14-placebo) was manufactured according to the procedure below:
(i) PEG400, DMSO, Transcutol HP and propylene glycol were weighed into a suitably sized vessel, vortexed briefly and mixed until clear.
(ii) For NA14 only: Acyclovir was added to the vessel from Step (i) and stirred at approximately 900 rpm with a magnetic stirrer bar until visibly dissolved.
(iii) HPC MF was weighed into a suitably sized vessel and slowly added to the vessel from Step (ii) for NA14 or Step (i) for NA14-placebo whilst stirring at 1500 rpm in order to create a vortex.
(iv) The formulation from Step (iii) was then stirred until the gelling agent was fully solvated.

The drug content and purity of the four formulations AG21, AG23, EG04, and NA14 were confirmed to be within the expected range (95-105% area) using HPLC. There were no API crystals or excipient particulates noted in any of the formulations tested by microscopic observations. The emulsified gel (EG04) was observed to have regular droplet size and uniform distribution of the emulsion. The apparent pH of the formulations ranged between 6.01 and 6.51 for the formulations which were pH adjusted to between pH 6 and 6.5 (AG21, AG23, EG04, AG21-placebo, AG23-placebo, and EG04-placebo), and between 8.31 and 8.98 for NA14 and NA14-placebo.

TABLE 11

Composition of formulations containing acyclovir

| Excipient | AG21 | AG21-placebo | AG23 | AG23-placebo | EG04 | EG04-placebo | NA14 | NA14-placebo |
|---|---|---|---|---|---|---|---|---|
| Acyclovir | 0.20 | — | 0.20 | — | 0.18 | — | 0.16 | — |
| Water | 29.30 | 29.50 | 29.45 | 29.65 | 24.17 | 24.35 | — | — |
| DMSO | — | — | — | — | — | — | 10.00 | 10.00 |
| PEG 400 | 9.10 | 9.10 | 11.69 | 11.69 | 7.81 | 7.81 | 53.84 | 54.00 |
| Phenoxyethanol | 1.00 | 1.00 | 1.00 | 1.00 | 1.00 | 1.00 | — | — |
| Propylene glycol | — | — | 19.06 | 19.06 | — | — | 10.00 | 10.00 |
| Transcutol ® HP | 49.90 | 49.90 | 28.25 | 28.25 | 42.84 | 42.84 | 25.00 | 25.00 |
| Carbopol ® 980 | 0.50 | 0.50 | 0.35 | 0.35 | — | — | — | — |
| Sepineo ™ P600 | — | — | — | — | 4.00 | 4.00 | — | — |
| Crodamol ™ GTCC | — | — | — | — | 10.00 | 10.00 | — | — |
| HPC MF | — | — | — | — | — | — | 1.00 | 1.00 |
| Total before pH adjustment | 90.00 | 90.00 | 90.00 | 90.00 | 90.00 | 90.00 | N/A | N/A |
| 0.2M NaOH | | | To pH 6-6.5 | | | | — | — |
| Water (2$^{nd}$ addition) | | | Q.S 100% | | | | — | — |
| Total | 100.00 | 100.00 | 100.00 | 100.00 | 100.00 | 100.00 | 100.00 | 100.00 |

— = not included
N/A = not applicable

Example 7. In Vivo Pig Skin Studies of Selected Formulations

This Example was to compare 4 topical acyclovir formulations (AG21, AG23, EG04, and NA14) with Zovirax® Cream 5% in the skin of 3 pigs in-vivo 12-24 h post-dose using the methodology of dermal open flow microperfusion (dOFM).

dOFM is a minimally invasive method for continuous sampling of interstitial fluid (ISF) in dermal tissue and offers the possibility to investigate the penetration of topical products into the dermis. See e.g., Bodenlenz, M. et al. *Clin. Pharmacokinet* 56:91-98 (2017). The pharmacokinetics as well as the pharmacodynamics of the active pharmacokinetic (PK) ingredients can be visualized in a time-resolved manner. No pharmacodynamic endpoint is evaluated in the present study.

The study was performed in three young (2-3 months) Landrace pigs. The dermal ISF concentrations of acyclovir on day 2 after topical application (0 h) of four different formulations and the originator (Zovirax® Cream 5%) were assessed for 12 hours (12-24 h) using continuous interstitial fluid sampling by dOFM. During the dOFM-sampling periods the products were to be re-applied in intervals of 2 hours (12 h, 14 h, 16 h, 18 h, 20 h, 22 h). Each dosing contains 10 mg/cm$^2$ formulation. At the end of the 12-hour dOFM sampling period the animals were to be euthanized. Moreover, two blood samples were to be taken at the start of dOFM sampling on day 2 (12 h) and the end (24 h) of the dOFM-sampling period to investigate potential carry-over effects between systemic and dermal concentrations.

On day 1 the pigs were to be anesthetized using e.g. isofluran inhalation. The skin of the pigs were to be cleaned with gauze and water. Ten application sites were to be demarcated by an indelible marker on the back of the animal. Each application site was to have an area of 10 cm$^2$ (2.5 cm×4 cm). The probe insertion areas next to the treatment sites were to be covered with a transparent medical film (Opsite flexifix, smith&nephew, England) to avoid contamination with the test product. Before dosing of the test products, the skin barrier in the topical application areas were to be characterized by TEWL (transepidermal water loss, measured by Aquaflux 200 device, Biox Ldt, London UK). The formulations were to be dosed, and after dosing the application sites were to be covered using a non-occlusive cover to avoid damage/contamination of the skin by contact to objects/ground in the pig shed and to reduce smearing and environmental contamination of the skin. To avoid a removal of the non-occlusive covers a tight fabric were to be put on the pig.

On day 2 the anesthesia of the pigs were to be started first. The tight fabric and the covering were to be removed from the topical treatment sites. To avoid contamination of the dOFM probes with residual drug on the skin surface while inserting the probes, the needle puncture sites next to the treatment sites were to be cleaned following a defined procedure: first, the skin next to the sites were to be cleaned using gauze soaked with water; second, after drying the skin with gauze, tape stripping were to be performed with highly adhesive tape to remove the potentially contaminated layers of stratum corneum at the insertion points.

Afterwards 3 dOFM probes per treatment site were to be inserted into the dermal layer of the skin at a distance of ~10 mm and a mean depth of approximately 1.5±0.30 mm. Actual dOFM probe depth assessments were to be measured by ultrasound. After insertion, dOFM-probes are flushed for 10 minutes with a flow rate of 10 µl/min. dOFM sampling were to be performed continuously with a flow rate of 1 µl/min. A baseline sample (≥30 min) were to be collected prior to the dosing at 12 hours (dose 2).

In the OFM-sampling period the sample containers were to be exchanged at least hourly for 12 hours. During this period the formulations were to be re-applied to the respective application site in 2-hour intervals (topical doses 3-7). The sampling/dosing schedule is shown in FIG. 4. Samples were to be pooled per treatment site, thus obtaining 1 pooled sample for analysis per site and interval to show interstitial PK over a 12-hour duration (12-24 h).

The test topical acyclovir formulations (AG21, AG23, EG04, and NA14) and Zovirax® Cream 5% were to be applied by positive displacement pipette followed by spreading evenly on the application site. Before applying next dose, the remaining study medication were to be removed by wiping the application site with a clean gauze pad from the top to the middle and from the bottom to the middle once.

dOFM sampling were be performed with standard OFM perfusate, Elomel isoton (Fresenius Kabi Austria)+2% Human Serum Albumin.

The results were shown in FIGS. 5 and 6. As can be seen from FIGS. 5 and 6, compared to the other tested formulations, AG21 unexpectedly shows a much higher penetration into the dermal interstitial space as evidenced by the much higher observed AUC and acyclovir concentrations during the course of this study.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

With respect to aspects of the invention described as a genus, all individual species are individually considered separate aspects of the invention. If aspects of the invention are described as "comprising" a feature, embodiments also are contemplated "consisting of" or "consisting essentially of" the feature.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference. To the extent that any meaning or definition of a term in this document conflicts with any meaning or definition of the same term in a document incorporated by reference, the meaning or definition assigned to that term in this document shall govern.

What is claimed is:

1. An aqueous gel formulation comprising: a) acyclovir in an amount of 0.1% to 0.3% by weight of the aqueous gel formulation; b) water; c) diethylene glycol monoethyl ether; d) PEG 400; e) a gel-forming agent which is a crosslinked polyacrylic acid; and f) an antioxidant or preservative, wherein the aqueous gel formulation is substantially free of acyclovir in a solid form, wherein the aqueous gel formulation comprises by weight of the aqueous gel formulation, water in an amount of 35-45%, diethylene glycol monoethyl ether in an amount of 45-55%, and PEG 400 in an amount of 5-15% and wherein the pH of the aqueous gel formulation is about 4 to 8.

2. The aqueous gel formulation of claim 1, wherein acyclovir is the only active ingredient.

3. The aqueous gel formulation of claim 1, wherein the antioxidant or preservative is selected from butylated hydroxytoluene, phenoxyethanol, sodium metabisulfite, EDTA, ascorbic acid, and combinations thereof.

4. The aqueous gel formulation of claim 1, wherein the aqueous gel formulation comprises by weight of the aqueous gel formulation, water in an amount of 39.3%, diethylene glycol monoethyl ether in an amount of 49.9%, and PEG 400 in an amount of 9.1%.

* * * * *